United States Patent
Kwon et al.

(10) Patent No.: US 11,981,618 B2
(45) Date of Patent: May 14, 2024

(54) P62 LIGAND COMPOUND, AND COMPOSITION FOR PREVENTING, AMELIORATING OR TREATING PROTEINOPATHIES COMPRISING THE SAME

(71) Applicant: AUTOTAC INC., Seoul (KR)

(72) Inventors: Yong Tae Kwon, Seoul (KR); Chang Hoon Ji, Seoul (KR); Srinivasrao Ganipisetti, Seoul (KR); Hee Yeon Kim, Seoul (KR); Su Ran Mun, Seoul (KR); Chan Hoon Jung, Seoul (KR); Eui Jung Jung, Seoul (KR); Ki Woon Sung, Seoul (KR)

(73) Assignee: AUTOTAC INC., Seoul (KR)

(*) Notice: Subject to any disclaimer, the term of this patent is extended or adjusted under 35 U.S.C. 154(b) by 198 days.

(21) Appl. No.: 17/262,129

(22) PCT Filed: Jul. 24, 2019

(86) PCT No.: PCT/KR2019/009203
§ 371 (c)(1),
(2) Date: Jan. 21, 2021

(87) PCT Pub. No.: WO2020/022783
PCT Pub. Date: Jan. 30, 2020

(65) Prior Publication Data
US 2021/0347749 A1 Nov. 11, 2021

Related U.S. Application Data

(60) Provisional application No. 62/702,473, filed on Jul. 24, 2018.

(51) Int. Cl.
*C07C 217/58* (2006.01)
*A23L 33/10* (2016.01)
(Continued)

(52) U.S. Cl.
CPC ........... *C07C 217/58* (2013.01); *A23L 33/10* (2016.08); *A61K 31/05* (2013.01); *A61K 31/12* (2013.01);
(Continued)

(58) Field of Classification Search
CPC ..... C07C 217/58; C07C 43/23; C07C 47/575; C07C 235/06; C07C 237/06;
(Continued)

(56) References Cited

U.S. PATENT DOCUMENTS 4,167,581 A   9/1979  Smith
4,471,116 A * 9/1984  Davidson .............. C07C 217/62
                                                    544/43

(Continued)

FOREIGN PATENT DOCUMENTS

CN   102229602 A   11/2011
CN   107848932 A    3/2018
(Continued)

OTHER PUBLICATIONS

PCT Search Report & Written Opinion for PCT/KR2019/009203, dated Nov. 11, 2019.
(Continued)

*Primary Examiner* — Taylor V Oh
(74) *Attorney, Agent, or Firm* — Sughrue Mion, PLLC

(57) ABSTRACT

The present invention relates to a novel p62 ligand compound, a stereoisomer, hydrate, solvate or prodrug thereof, and a pharmaceutical or food composition for preventing or treating proteinopathies comprising the same as an active ingredient. The p62 ligand compound according to the present invention can be usefully used as a pharmaceutical composition for the prevention, amelioration or treatment of
(Continued)

various proteinopathies by activating autophagy in cells and thus selectively eliminating in vivo proteins, organelles and aggregates.

12 Claims, 12 Drawing Sheets

(51) Int. Cl.
| | |
|---|---|
| A61K 31/05 | (2006.01) |
| A61K 31/12 | (2006.01) |
| A61K 31/138 | (2006.01) |
| A61K 31/166 | (2006.01) |
| A61K 31/192 | (2006.01) |
| A61K 31/277 | (2006.01) |
| A61K 31/336 | (2006.01) |
| A61K 31/355 | (2006.01) |
| A61K 31/4015 | (2006.01) |
| A61K 31/4155 | (2006.01) |
| A61K 31/4184 | (2006.01) |
| A61K 31/421 | (2006.01) |
| A61K 31/428 | (2006.01) |
| A61K 31/4535 | (2006.01) |
| A61K 31/4709 | (2006.01) |
| A61K 31/4745 | (2006.01) |
| A61K 31/496 | (2006.01) |
| A61K 31/50 | (2006.01) |
| A61K 31/5025 | (2006.01) |
| A61K 31/506 | (2006.01) |
| A61K 31/517 | (2006.01) |
| A61K 31/5377 | (2006.01) |
| A61K 31/5415 | (2006.01) |
| A61K 31/551 | (2006.01) |
| A61K 31/565 | (2006.01) |
| A61K 39/395 | (2006.01) |
| A61K 47/54 | (2017.01) |
| A61K 47/55 | (2017.01) |
| A61K 47/68 | (2017.01) |
| A61P 25/28 | (2006.01) |
| C07C 43/23 | (2006.01) |
| C07C 47/575 | (2006.01) |
| C07C 235/06 | (2006.01) |
| C07C 237/06 | (2006.01) |
| C07C 275/24 | (2006.01) |
| C07C 279/12 | (2006.01) |
| C07D 303/18 | (2006.01) |

(52) U.S. Cl.
CPC .......... *A61K 31/138* (2013.01); *A61K 31/166* (2013.01); *A61K 31/192* (2013.01); *A61K 31/277* (2013.01); *A61K 31/336* (2013.01); *A61K 31/355* (2013.01); *A61K 31/4015* (2013.01); *A61K 31/4155* (2013.01); *A61K 31/4184* (2013.01); *A61K 31/421* (2013.01); *A61K 31/428* (2013.01); *A61K 31/4535* (2013.01); *A61K 31/4709* (2013.01); *A61K 31/4745* (2013.01); *A61K 31/496* (2013.01); *A61K 31/50* (2013.01); *A61K 31/5025* (2013.01); *A61K 31/506* (2013.01); *A61K 31/517* (2013.01); *A61K 31/5377* (2013.01); *A61K 31/5415* (2013.01); *A61K 31/551* (2013.01); *A61K 31/565* (2013.01); *A61K 39/3955* (2013.01); *A61K 47/54* (2017.08); *A61K 47/55* (2017.08); *A61K 47/6803* (2017.08); *A61K 47/6849* (2017.08); *A61P 25/28* (2018.01); *C07C 43/23* (2013.01); *C07C 47/575* (2013.01); *C07C 235/06* (2013.01); *C07C 237/06* (2013.01); *C07C 275/24* (2013.01); *C07C 279/12* (2013.01); *C07D 303/18* (2013.01); *C07B 2200/07* (2013.01)

(58) Field of Classification Search
CPC ... C07C 275/24; C07C 279/12; C07C 217/34; C07C 229/12; C07C 235/08; C07C 235/34; C07C 275/10; C07C 279/08; C07C 279/10; C07C 403/18; C07C 237/20; A23L 33/10; A61K 31/05; A61K 31/12; A61K 31/138; A61K 31/166; A61K 31/192; A61K 31/277; A61K 31/336; A61K 31/355; A61K 31/4015; A61K 31/4155; A61K 31/4184; A61K 31/421; A61K 31/428; A61K 31/4535; A61K 31/4709; A61K 31/4745; A61K 31/496; A61K 31/50; A61K 31/5025; A61K 31/506; A61K 31/517; A61K 31/5377; A61K 31/5415; A61K 31/551; A61K 31/565; A61K 39/3955; A61K 47/54; A61K 47/55; A61K 47/6803; A61K 47/6849; A61K 31/135; A61K 31/165; A61K 31/155; A61K 31/17; A61P 25/28; A61P 25/00; A61P 35/00; A61P 3/10; A61P 27/02; C07D 303/18; C07D 263/44; C07D 405/14; C07D 405/04; C07B 2200/07; Y02A 50/30
USPC ........................................................ 514/475
See application file for complete search history.

(56) References Cited

U.S. PATENT DOCUMENTS

| | | | |
|---|---|---|---|
| 4,857,522 | A | 8/1989 | Dipietro et al. |
| 2004/0009932 | A1 | 1/2004 | Phelan et al. |
| 2015/0175607 | A1 | 6/2015 | Xie et al. |
| 2016/0031799 | A1 | 2/2016 | Xie et al. |
| 2018/0243244 | A1 | 8/2018 | Kwon et al. |
| 2018/0265452 | A1 | 9/2018 | Xie |
| 2021/0024454 | A1 | 1/2021 | Kwon et al. |
| 2021/0163399 | A1 | 6/2021 | Kwon et al. |
| 2021/0299253 | A1 | 9/2021 | Kwon et al. |

FOREIGN PATENT DOCUMENTS

| | | |
|---|---|---|
| CN | 112105598 A | 12/2020 |
| EP | 3338787 A1 | 6/2018 |
| KR | 10-2015-0039894 A | 4/2015 |
| KR | 10-2017-0021525 | 2/2017 |
| KR | 10-2017-0023045 | 3/2017 |
| KR | 10-2149539 B1 | 8/2020 |
| KR | 10-2154294 B1 | 9/2020 |
| WO | WO2013-022919 | 2/2013 |
| WO | 2015/031710 A1 | 3/2015 |
| WO | WO2016-200827 | 12/2016 |
| WO | WO2017-030292 | 2/2017 |
| WO | WO2017-079267 | 5/2017 |

OTHER PUBLICATIONS

Ciechanover, A. & Kwon, Y.T., Exp Mol Med 47, e147 (2015).
Dikic, I. & Elazar, Z., Nat Rev Mol Cell Biol 19, 349-364 (2018).
Caccamo, A., Majumder, S., Richardson, A., Strong, R. & Oddo, S., J Biol Chem 285, 13107-20 (2010).
Ji, C.H. & Kwon, Y.T., Mol Cells 40, 441-449 (2017).
Jung, C. H., Ro, S. H., Cao, J., Otto, N. M. & Kim, D. H., Febs Lett 584, 1287-95 (2010).
Ravikumar, B., Duden, R. & Rubinsztein, D.C., Hum Mol Genet 11, 1107-17 (2002).
Rodriguez-Navarro, J.A. et al., Neurobiol Dis 39, 423-38 (2010).

(56) References Cited

OTHER PUBLICATIONS

Sriram, S.M. & Kwon, Y.T., Nat Struct Mol Biol 17, 1164-5 (2010).
Sriram, S.M., Kim, B.Y. & Kwon, Y.T., Nat Rev Mol Cell Biol 12, 735-47 (2011).
Tasaki, T. et al., Mol Cell Biol 25, 7120-36 (2005).
Webb, J.L., Ravikumar, B., Atkins, J., Skepper, J.N. & Rubinsztein, D.C., J Biol Chem 278, 25009-13 (2003).
Barlow, J.J. et al., "B-Adrenoceptor stimulant properties of amidoalkylaminosubstitutedaryl-2-ethanols and 1-(aryloxy)-2-propanols", Journal of Medicinal Chemistry, 1981, vol. 24, No. 3. pp 315-322.
Australian Office Action dated Aug. 29, 2022 in Australian Application (AU) No. 2019312065.
John W.A. Findlay et al., "Relationships between Immunogen Structure and Antisera Specificity in the Narcotic Alkaloid Series", Clinical Chemistry, 1981, vol. 27, No. 9, pp. 1524-1535 (12 pages total).
Maciej J. Stefanko et al., "Synthesis of functionalised polyethylene glycol derivatives of naproxen for biomedical applications", Tetrahedron, 2008, vol. 64, No. 44, pp. 10132-10139 (8 pages total).
Nicolai Stuhr-Hansen et al., "Synthesis of Symmetrical and Non-Symmetrical Bivalent Neurotransmitter Ligands", ChemistrySelect, 2016, vol. 1, No. 3, pp. 407-413 (7 pages total).
REGISTRY(STN) [online], Nov. 16, 1984, CAS Registration No. 51169-99-4 (1 page total).
REGISTRY(STN) [online], Nov. 16, 1984, CAS Registration No. 47689-63-4 (1 page total).
REGISTRY(STN) [online], Jul. 27, 2004, CAS Registration No. 717091-45-7 (1 page total).
Kaiser, C. et al., "Adrenergic agents. 4. Substituted phenoxypropanolamine derivatives as potential β-adrenergic agonists," Journal of Medicinal Chemistry, 1977, vol. 20, No. 5, pp. 687-692 (6 pages total).
Yadav, J. S. et al., "An efficient protocol for regioselective ring opening of epoxides using samarium triflate: Synthesis of propranolol, atenolol and RO363," Journal of Molecular Catalysis A: Chemical, 2007, vol. 261, No. 2, pp. 207-212 (6 pages total).
Nelson, W. L. et al., "The 3, 4-Catechol derivative of propranolol, a minor dihydroxylated metabolite," Journal of Medicinal Chemistry, 1984, vol. 27, No. 7, pp. 857-861 (5 pages total).
Office Action dated Mar. 8, 2022 in Japanese Application No. 2021-503891.
International Search Report and Written Opinion of the International Searching Authority dated Nov. 11, 2019 in International Application No. PCT/KR2019/009204.
An et al., "Small-molecule PROTACs: An emerging and promising approach for the development of targeted therapy drugs", EBioMedicine, 2018, vol. 36, pp. 553-562.
Xiong et al., "LINC01857 as an oncogene regulates CREB1 activation by interacting with CREBBP in breast cancer", J. Cell. Physiol., 2019, pp. 1-9.
Bondeson et al., "Lessons in PROTAC design from selective degradation with a promiscuous warhead", Cell Chem Biol., 2018, vol. 25, No. 1, pp. 78-87 (28 pages total).
Puissant et al., "Resveratrol Promotes Autophagic Cell Death in Chronic Myelogenous Leukemia Cells via JNK-Mediated p62/SQSTM1 Expression and AMPK Activation", Cancer Research, 2010, vol. 70, No. 3, pp. 1042-1052.
International Search Report and Written Opinion of the International Searching Authority dated Nov. 11, 2019 in International Application No. PCT/KR2019/009205.
Teramachi et al., "Blocking the ZZ domain of sequestosome1/p62 suppresses myeloma growth and osteoclast formation in vitro and induces dramatic bone formation in myeloma-bearing bones in vivo", Leukemia, 2016, vol. 30, pp. 390-398.
Office Action dated Feb. 1, 2022 in Japanese Application No. 2021-503886.
Lei et al., "Targeting oncoproteins for degradation by small molecules in myeloid leukemia", Leukemia & Lymphoma, 2017, pp. 1-8 (9 pages total).
Yongtae Kwon, Autotac (Autophagy-targeting chimera) Technology, 2018, pp. 6-7 (7 pages total).
"CAS RN1181561-56-7", STN Registry Database, 2009 (3 pages total).
"CAS RN1181561-57-8", STN Registry Database, 2009 (4 pages total).
"CAS RN1217054-95-9", STN Registry Database, 2010 (3 pages total).
"CAS RN1869641-58-6", STN Registry Database, 2016 (4 pages total).
"CAS RN1874579-12-0", STN Registry Database, 2016 (3 pages total).
"CAS RN774192-20-0", STN Registry Database, 2004, (14 pages total).
"CAS RN87265-43-8", STN Registry Database, 1984 (5 pages total).
"CAS RN892571-80-1", STN Registry Database, 2006 (3 pages total).
"CAS RN892573-08-9", STN Registry Database, 2006 (4 pages total).
Keith D. Green et al., "Identification and Characterization of Inhibitors of the Aminoglycoside Resistance Acetyltransferase Eis from Mycobacterium tuberculosis", ChemMedChem, 2012, vol. 7, pp. 73-77 (5 pages total).
Ji et al., "The AUTOTAC chemical biology platform for targeted protein degradation via the autophagy-lysosome system", Nature Communications, (2022) 13:904 | https://doi.org/10.1038/s41467-022-28520-4 (14 pages).
Office Action dated Jul. 21, 2023 in Chinese Application No. 201980047607.6.
Communication dated Feb. 20, 2023, issued in Korean Application No. 10-2020-0092536.
Communication dated Feb. 20, 2023, issued in Korean Application No. 10-2020-0101379.
CAS Registry No. 1262521-61-8, 2011, 2 pages.
CAS Registry No. 562847-32-9, 2003, 1 page.
CAS Registry No. 99396-44-8, 1985, 2 pages.
CAS Registry No. 99342-74-2, 1985, 1 page.
CAS Registry No. 86955-68-2, 1984, 2 pages.
CAS Registry No. 77209-47-3, 1984, 1 page.
CAS Registry No. 76420-86-5, 1984, 2 pages.
CAS Registry No. 76420-85-4, 1984, 1 page.
CAS Registry No. 74867-70-2, 1984, 2 pages.
CAS Registry No. 58165-85-8, 1984, 1 page.
CAS Registry No. 2068956-48-7, 2017, 1 page.
CAS Registry No. 2000000-61-1, 2016, 1 page.
CAS Registry No. 1994480-74-8, 2016, 1 page.
CAS Registry No. 1881420-75-2, 2016, 1 page.
CAS Registry No. 1876857-32-7, 2016, 1 page.
CAS Registry No. 1874579-12-0, 2016, 2 pages.
CAS Registry No. 1869641-58-6, 2016, 1 page.
CAS Registry No. 1865340-43-7, 2016, 1 page.
CAS Registry No. 1859613-63-0, 2016, 1 page.
CAS Registry No. 1858409-61-6, 2016, 1 page.
CAS Registry No. 1827185-42-1, 2015, 1 page.
CAS Registry No. 1181454-24-9, 2009, 1 page.
CAS Registry No. 1181445-59-9, 2009, 1 page.
CAS Registry No. 940199-73-5, 2007, 1 page.
CAS Registry No. 892571-67-4, 2006, 1 page.
CAS Registry No. 861442-53-7, 2005, 1 page.
CAS Registry No. 861409-41-8, 2005, 1 page.
CAS Registry No. 774192-20-0, 2004, 1 page.
CAS Registry No. 190018-01-0, 1997, 1 page.
Office Action dated Dec. 18, 2023 by the United States Patent and Trademark Office in U.S. Appl. No. 17/262,157.
Bondeson et al., "Catalytic in vivo protein knockdown by small-molecule PROTACs", Nature Chemical Biology, 2015, vol. 11, pp. 611-617 (9 pages total).
Lu et al., "Hijacking the E3 Ubiquitin Ligase Cereblon to Efficiently Target BRD4", Chemistry & Biology, 2015, vol. 22, No. 6, pp. 755-763 (10 pages total).

(56) References Cited

OTHER PUBLICATIONS

Winter et al., "Phthalimide conjugation as a strategy for in vivo target protein degradation", Science, 2015, vol. 348, Issue. 6241, pp. 1376-1381 (7 pages total).

Islam et al., "Autophagic Regulation of p62 is Critical for Cancer Therapy" Int. J. Mol. Sci. 2018, vol. 19, No. 1405, pp. 1-15 (15 pages total).

* cited by examiner

[Fig. 1]
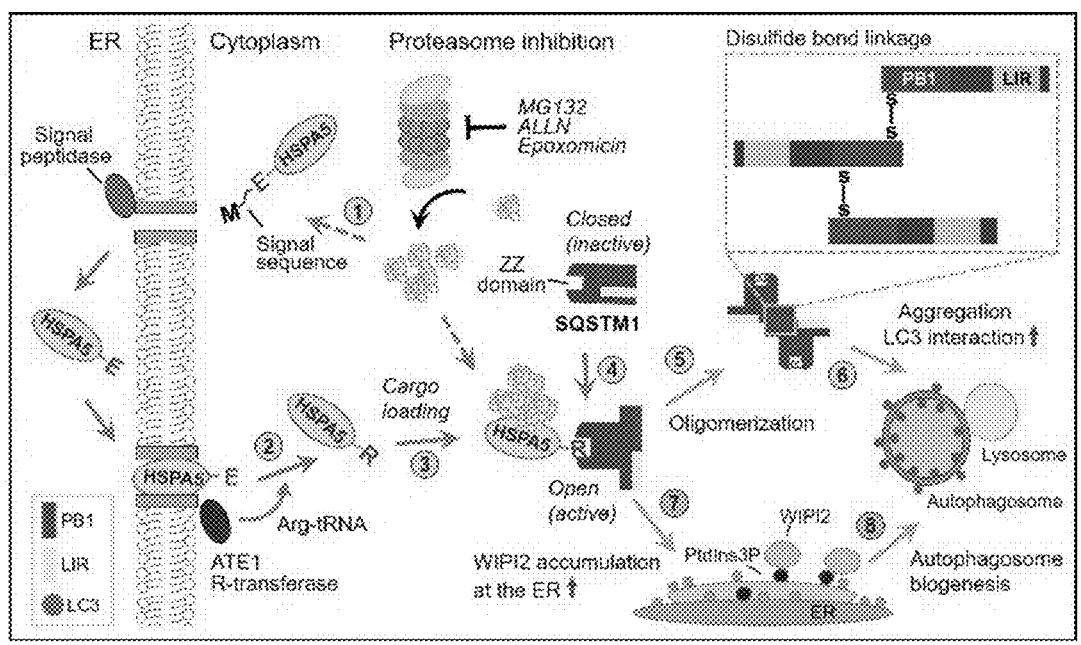

[Fig. 2]
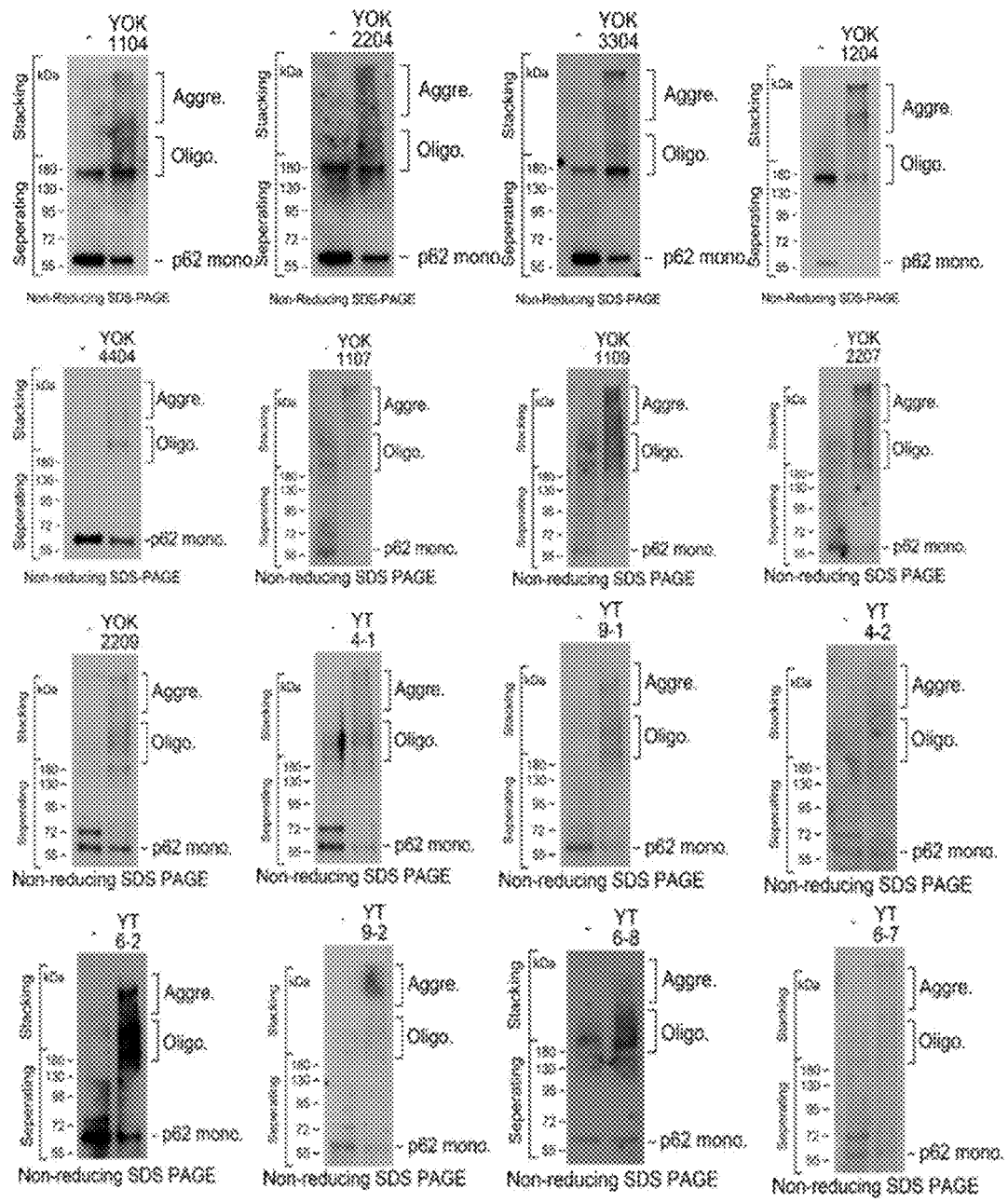

[Fig. 3]
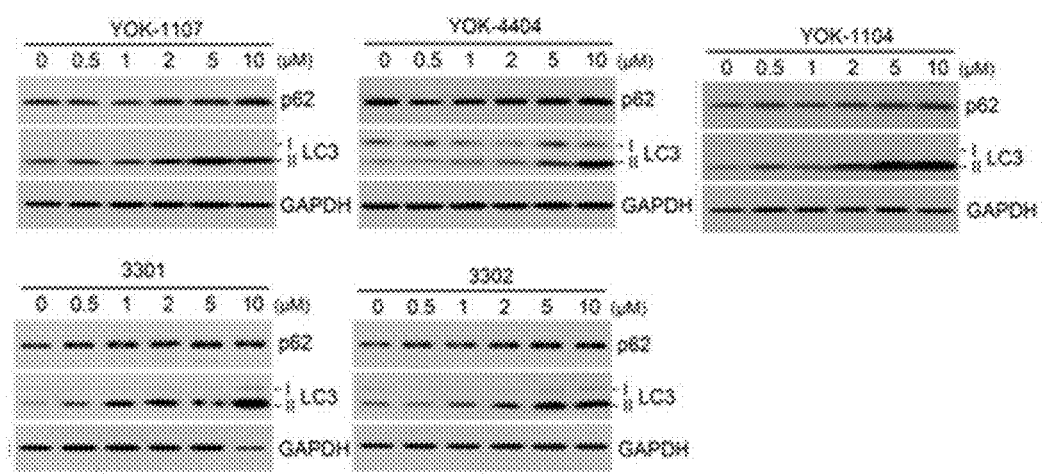

[Fig. 4]
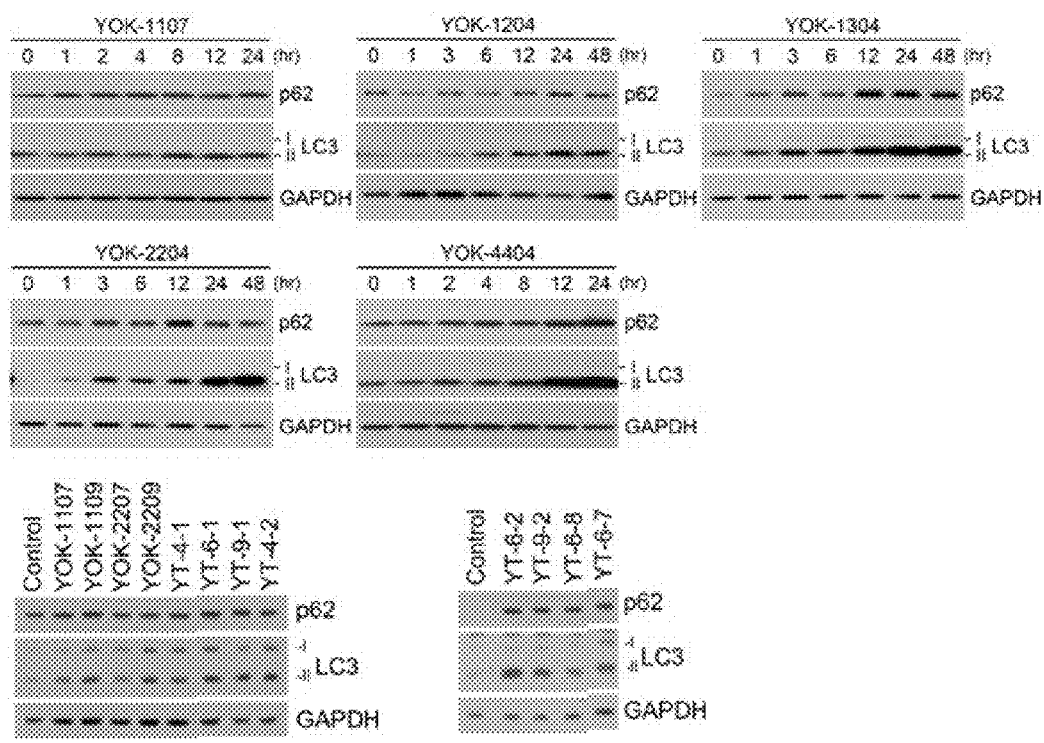

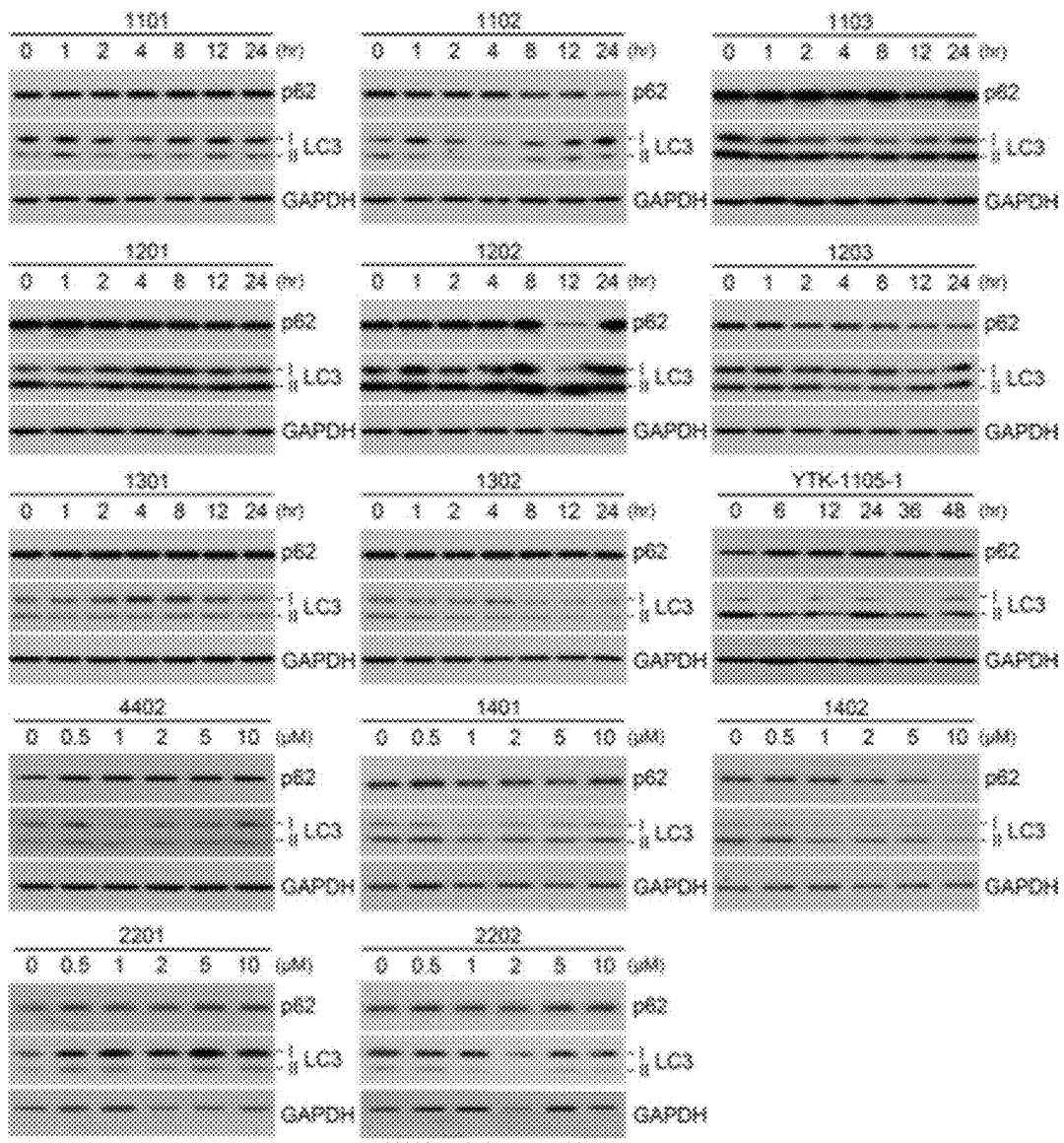
[Fig. 5]

[Fig. 6a]
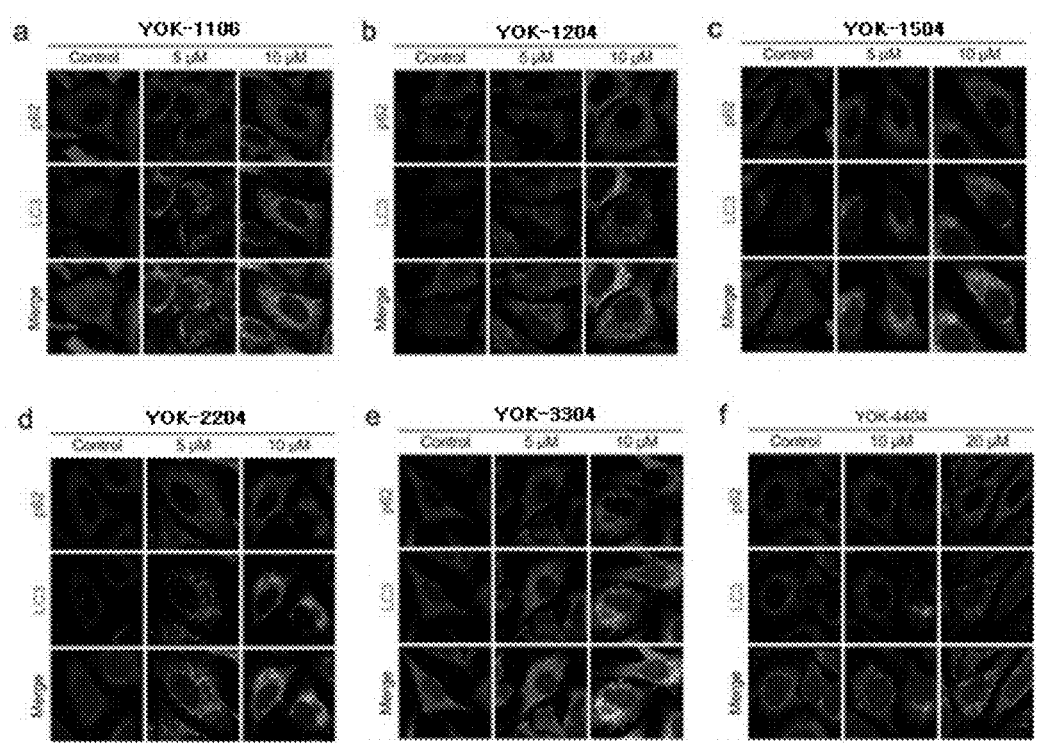

[Fig. 6b]
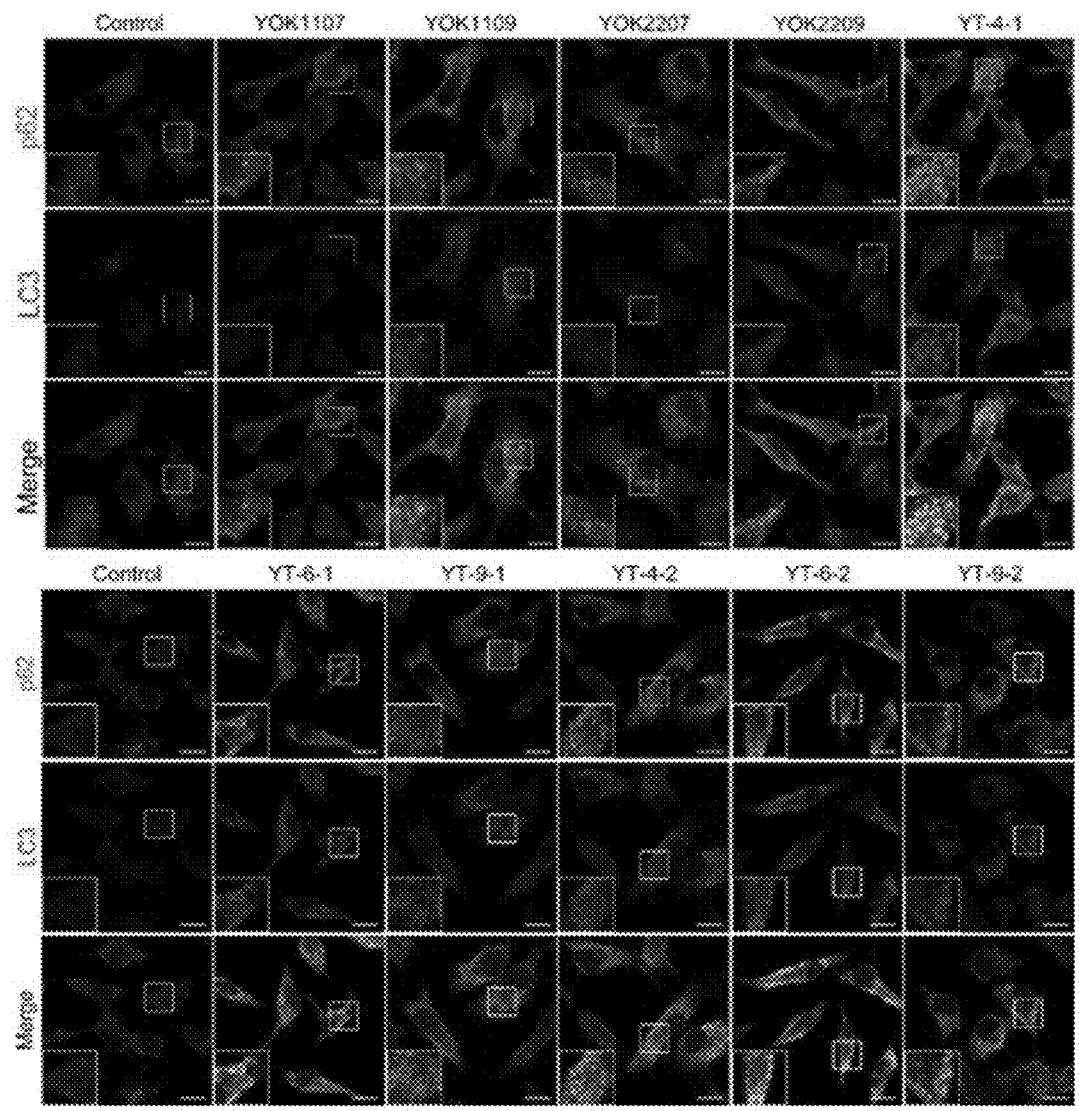

[Fig. 7]
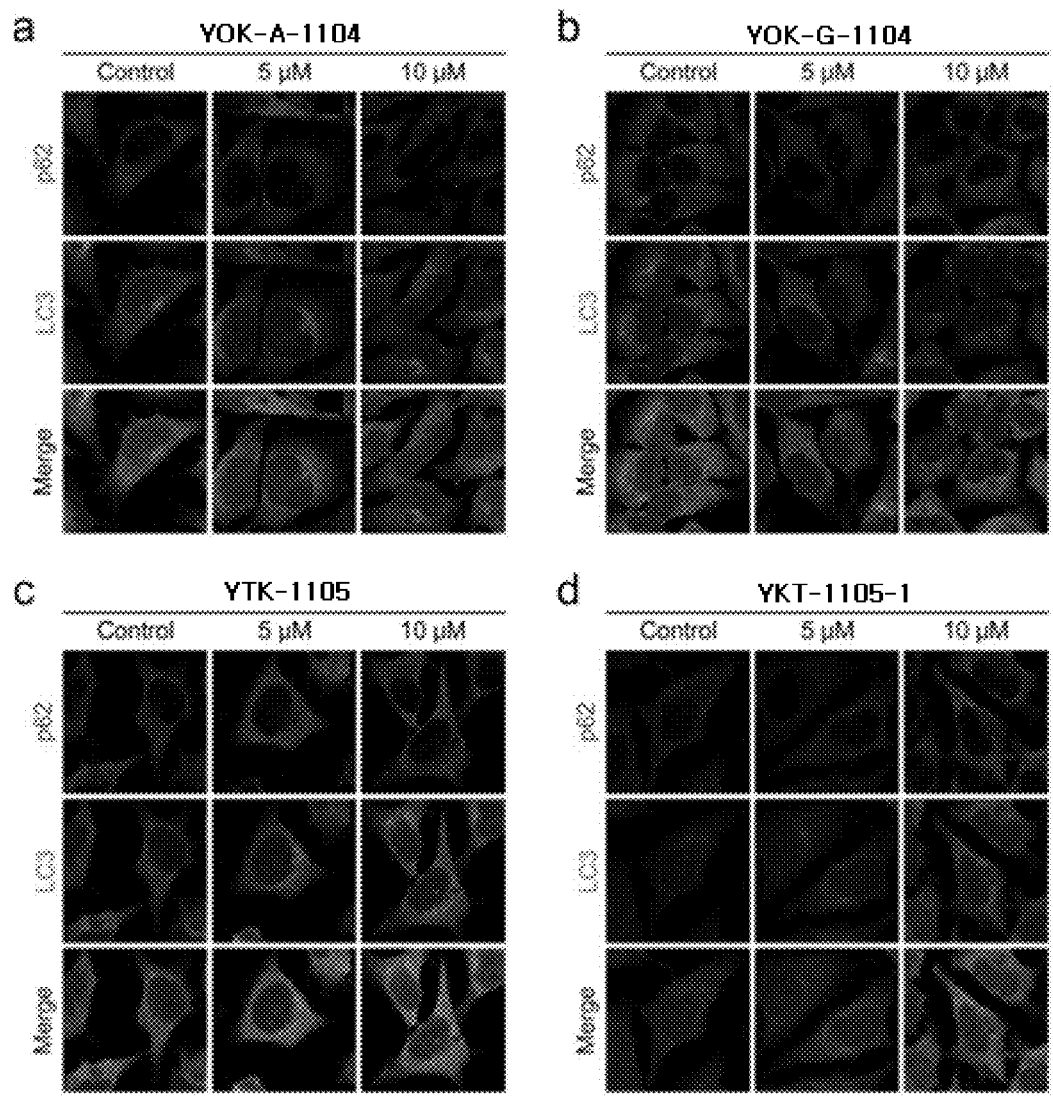

[Fig. 8a]
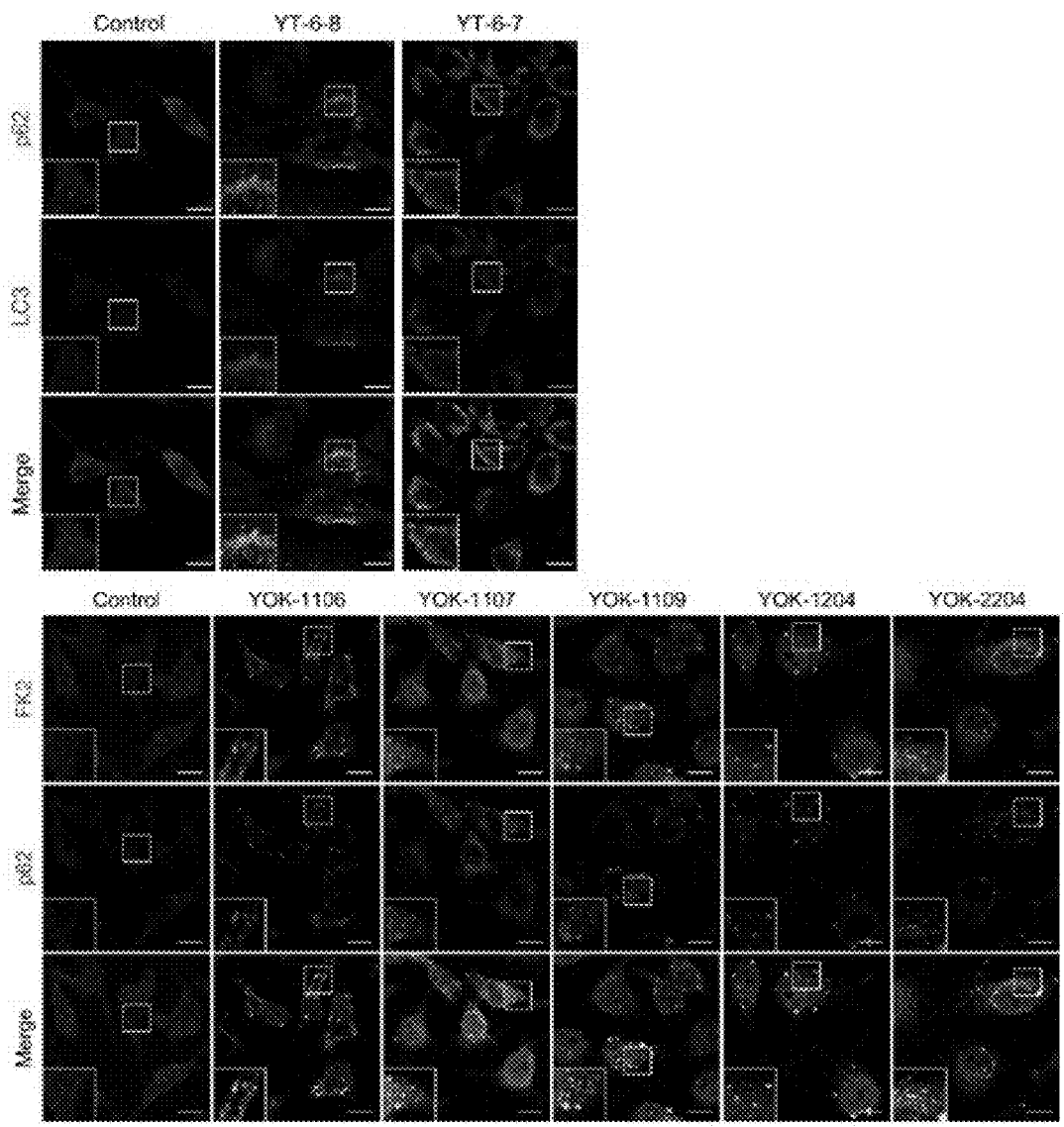

[Fig. 8b]
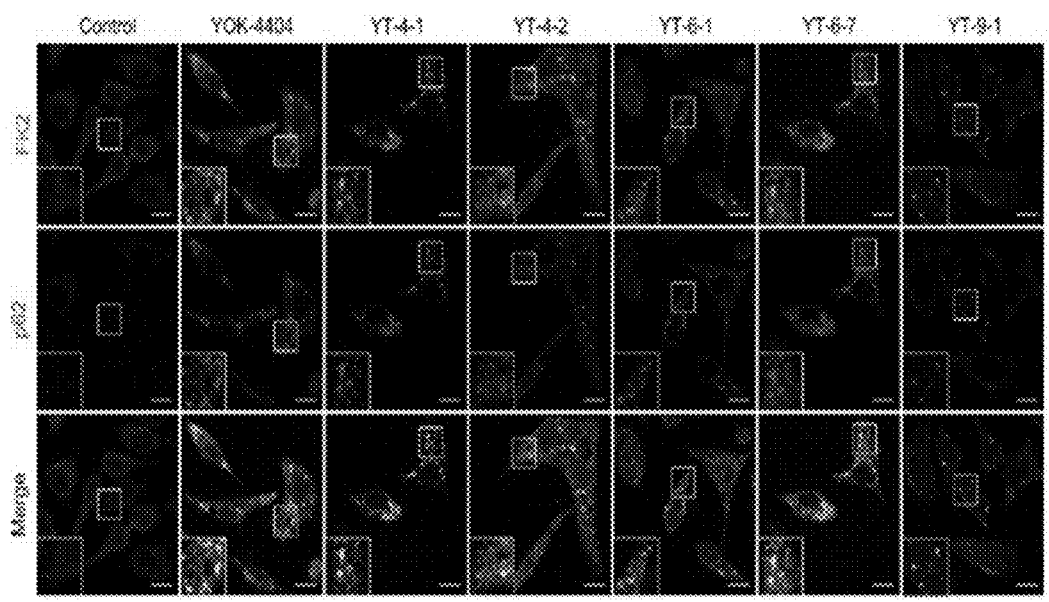

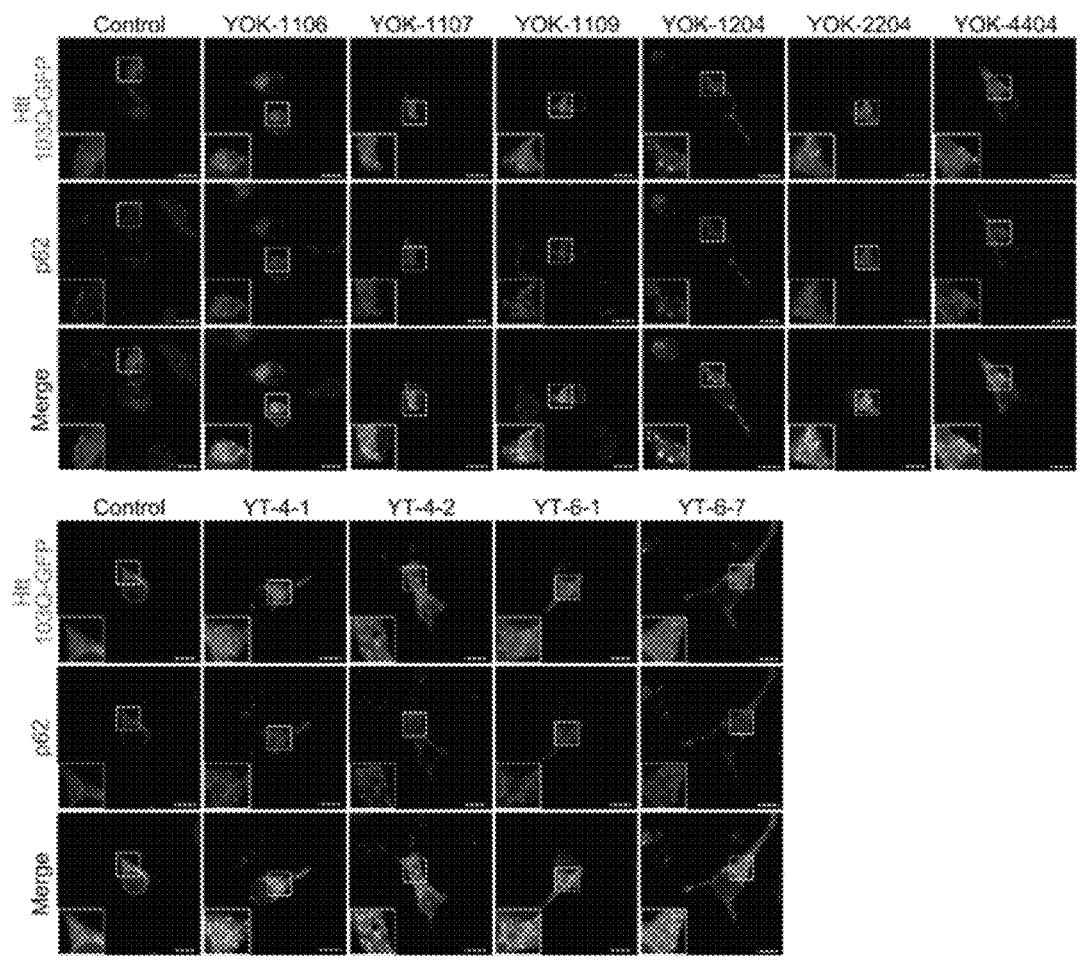
[Fig. 9a]

[Fig. 9b]
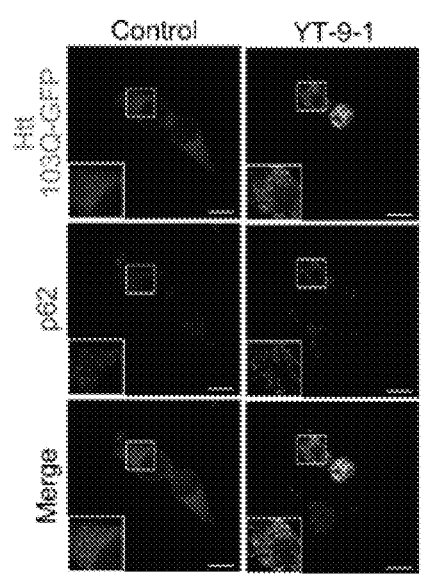

ional residues (Nt-Arg, Nt-Lys, Nt-His) such as N-terminal arginine resi-
P62 LIGAND COMPOUND, AND COMPOSITION FOR PREVENTING, AMELIORATING OR TREATING PROTEINOPATHIES COMPRISING THE SAME

REFERENCE TO RELATED APPLICATIONS

The present application is a National Stage Application of PCT Application No. PCT/KR2019/009203 filed on Jul. 24, 2019, which claims priority to Provisional U.S. Application No. 62/702,473, filed Jul. 24, 2018, which are incorporated herein in their entirety.

BACKGROUND OF THE INVENTION

(a) Field of the Invention

The present invention relates to a novel p62 ligand compound, and a pharmaceutical or food composition for preventing or treating proteinopathies comprising the same.

(b) Description of the Related Art

The N-end rule pathway is a proteolytic system where a specific N-terminal residue of a protein acts as a degradation signal (FIG. 1). The N-end rule degradation signal is exemplified by type I basic residues including N-terminal arginine (Nt-Arg), lysine (Nt-Lys) and histidine (Nt-His); and type II hydrophobic residues including phenylalanine (Nt-Phe) leucine (Nt-Leu), tryptophan (Nt-Trp), tyrosine (Nt-Tyr) and isoleucine (Nt-Ile). These N-terminal residues bind to specific N-recognins (hereinafter referred to as N-ligands).

The present inventors have first discovered or cloned previously known N-recognins, namely UBR1, UBR2, UBR4, and UBR5, and found that they utilize the UBR box as a substrate recognition domain (Tasaki, T. et al., Mol Cell Biol 25, 7120-36 (2005)). The present inventors have also found that the UBR box binds to type-I N-end rule ligands (Nt-Arg, Nt-Lys, Nt-His) such as N-terminal arginine residue to recognize a substrate and to link a ubiquitin chain to the substrate. It has further been found that UBR1 and UBR2 have an N-domain which plays an important role in the binding of type-2 N-end rule ligands (Nt-Trp, Nt-Phe, Nt-Tyr, Nt-Leu, and Nt-Ile) (Sriram, S. M., Kim, B. Y. & Kwon, Y. T., Nat Rev Mol Cell Biol 12, 735-47 (2011)). The ubiquitinized substrate produced from the binding between N-recognins and N-end rule ligands is delivered to proteasome where it is degraded into a short peptide. In this process, specific N-terminal residues (Nt-Arg, Nt-His, Nt-Lys, Nt-Trp, Nt-Phe, Nt-Tyr, Nt-Leu, Nt-Leu) are the essential determinants of binding since N-recognins provide most of the hydrogen bonds needed to target the N-end rule substrate (Sriram, S. M. & Kwon, Y. T., Nat Struct Mol Biol 17, 1164-5 (2010)).

If misfolded proteins that are poorly folded in cells linger for a prolonged time, they are aggregated and block proteasome functions or reduce other cellular functions which cause cytotoxic substances, and therefore, misfolded proteins are ubiquitinated by ubiquitin ligases and delivered to proteasomes for degradation (Ji, C. H. & Kwon, Y. T., Mol Cells 40, 441-449 (2017)). In normal cells, this process is smooth and minimizes damage caused by misfolded proteins, whereas in aged neurons, this process is slowed so that the ubiquitinated misfolded proteins accumulate and these surplus protein wastes are converted back into aggregates (Ciechanover, A. & Kwon, Y. T., Exp Mol Med 47, e147 (2015)). In addition, neuronal cells of patients with degenerative brain diseases such as Huntington's disease, Parkinson's disease, human mad cow disease, and Lou Gehrig's disease even among proteinopathies, have strong properties that specific mutant proteins are transformed into aggregates, and thus are not degraded by the proteasome described above. The reason is that since the proteasome has a narrow inner diameter of about 13 Angstroms, the misfolded proteins must be unfolded, and when the proteins are aggregated, they will not be unfolded.

Meanwhile, autophagy is a major intracellular protein degradation system along with the ubiquitin-proteasome system. Autophagy is a protein degradation process essential to maintain cell homeostasis and genetic stability by degrading aged or impaired cellular organelles or damaged or abnormally folded proteins (Ji, C. H. & Kwon, Mol Cells 40, 441-449 (2017)). In particular, when misfolded protein aggregates are accumulated in a cytoplasm, they can become cytotoxic substances, and thus, should be received and degraded by autophagy. The mechanism for autophagy is largely divided into macroautophagy, microautophagy and chaperone-mediated autophagy, and it is divided into bulk autophagy and selective autophagy, depending on the purpose of degrading the intracellular substrate (Dikic, I. & Elazar, Z., Nat Rev Mol Cell Biol 19, 349-364 (2018)). Of these, selective autophagy and chaperone-mediated autophagy cause selective degradation of unwanted intracellular proteins and dysfunctional organelles. By inducing selective autophagy, the development of new therapies for diseases based on the accumulation of pathologically misfolded proteins and dysfunctional organelles is currently building a new paradigm. p62/SQSTM1/Sequestosome-1 protein is important for initiating the formation of autophagosome which is a mediator in the mechanism of selective autophagy, and delivering the contents. At this time, p62/SQRSM1/Sequestosome-1 bind to the misfolded proteins and their aggregates, which are delivered to autophagosome. P62 undergoes self-oligomerization as a key process when delivering misfolded proteins to autophagosomes (Ji and Kwon, Y. T., Mol Cells 40, 441-449 (2017)). At this time, the misfolded proteins are concentrated together to reduce the volume, thereby facilitating degradation by autophagy. PB1 domain mediates the self-oligomerization of p62, but the regulatory mechanism thereof is not well known. The misfolded protein-p62 conjugate delivered to autophagosome can be degraded by lysosomal enzymes as the autophagosome binds to a lysosome. Through the mechanism described above, autophagy is important for maintaining cell homeostasis by regulating intracellular changes in damaged proteins and cellular organelles. When autophagic function is weakened, it leads to the accumulation and aggregation of the misfolded proteins, which results in proteinopathies (Ciechanover, A. & Kwon, Y. T., Exp Mol Med 47, e147 (2015)). A key technique of the present invention is to provide a method for effectively eliminating misfolded proteins or its aggregates, which cause proteinopathies. For this purpose, it is necessary to activate only selective autophagy without activating bulk autophagy that have a wide range of effects on various biological pathways.

Studies on the activation of autophagy to treat proteinopathies have been actively conducted. A regulator that normally inhibits bulk autophagy is mTOR. A method of activating autophagy using mTOR inhibitors is most widely used (Jung, C. H., Ro, S. H., Cao, J., Otto, N. M. & Kim, D. H., FEBS Lett 584, 1287-95 (2010)). Specifically, by using rapamycin treatment, amyloid beta (Ab) and tau were eliminated and simultaneously cognitive ability was improved in an AD animal model over-expressing APP (Caccamo, A., Majumder, S., Richardson, A., Strong, R. & Oddo, S., J Biol Chem 285, 13107-20 (2010)); tau was eliminated in an AD animal model over-expressing tau (Rodriguez-Navarro, J. A. et al., Neurobiol Dis 39, 423-38 (2010)); and the over-expressed mutant alpha-synuclein protein aggregate was eliminated in a PD mouse model (Webb, J. L., Ravikumar, B., Atkins, J., Skepper, J. N. & Rubinsztein, D. C., J Biol Chem 278, 25009-13 (2003)). It was confirmed that in a HD mouse, huntingtin aggregates were efficiently eliminated by using CCI-779, a rapamycin-like substance, improving animal behavior and cognitive ability (Ravikumar, B., Duden, R. & Rubinsztein, D. C., Hum Mol Genet 11, 1107-17 (2002)). However, mTOR plays a very important role in various intracellular pathways including NF-kB. Therefore, although it exhibits excellent activity to eliminate the misfolded protein aggregate of proteinopathic diseases, there is a limitation in that these bulk autophagy activators, which are known that mTOR is a drug target, are used as therapeutic agents.

As described above, currently, there is no effective therapeutic agent to treat most proteinopathies. In the case of ubiquitin ligase ligand for the elimination of misfolded proteins which are the main cause, it is difficult to eliminate them when the misfolded proteins are aggregated. In addition, mTOR inhibitors, which are the most commonly used compounds as bulk autophagy activators, play a wide role in regulating overall gene expression in cells in response to stimuli from a variety of external environments in addition to the regulation of autophagy, and thus, they have the disadvantage in terms of being unsuitable as a therapeutic agent. Therefore, there is a need to develop a method for eliminating misfolded protein aggregates by activating p62, a key regulator of selective autophagy, without lowering the activity of mTOR, a regulator of the bulk autophagy.

SUMMARY OF THE INVENTION

Under these circumstances, the present inventors have conducted intensive studies to discover a prophylactic and therapeutic agent for proteinopathies using a material that activates autophagy independently of mTOR, and as a result, have found that ligands binding to p62, more specifically to the ZZ domain of p62, bind to LC3 and activate autophagy, resulting in the effective elimination of the pathogenic protein aggregates such as mutant huntingtin and alpha-synuclein, and thereby, it can be used for the prevention, amelioration or treatment of various proteinopathies. The present invention has been completed on the basis of such findings.

It is an object of the present invention to provide a novel p62 ligand compound which induces activation and oligomerization of p62 protein.

It is another object of the present invention to provide a method for delivering p62 and a misfolded protein to which p62 is bound, to an autophagosome and finally delivering them to a lysosome for elimination by using the aforementioned novel compound.

It is another object of the present invention to provide a method for increasing macroautophagy activity through p62 protein by using the aforementioned novel compound.

It is still another object of the present invention to provide a pharmaceutical or food composition for eliminating a misfolded protein aggregate comprising the aforementioned novel compound as an active ingredient.

It is the other object of the present invention to provide a pharmaceutical or food composition for the prevention, amelioration or treatment of proteinopathies comprising the aforementioned novel compound as an active ingredient.

In order to achieve the above objects, one embodiment of the present invention provides a novel compound that acts as a ligand of the p62 protein. Preferably, the novel p62 ligand according to the invention binds to the ZZ domain of p62.

Another embodiment of the present invention provides a pharmaceutical composition for the prevention and treatment of proteinopathies such as neurodegenerative diseases, or a health functional food for the prevention or amelioration of proteinopathies, comprising a ligand binding to the ZZ domain of p62 protein as an active ingredient.

Another embodiment of the present invention provides (1) a method of inducing p62 oligomerization and structural activation; (2) a method of increasing p62-LC3 binding; (3) a method of increasing the delivery of p62 to autophagosome; (4) a method of activating autophagy; and (5) a method of eliminating misfolded protein aggregates, the method including the step of treating a cell or a p62 protein with the ligand that binds to the ZZ domain of p62.

Still another embodiment of the present invention provides a technique for eliminating misfolded protein aggregates, which are a causative factor of degenerative brain diseases, by activating p62 which delivers the misfolded protein aggregates directly to an autophagosome.

A key technique of the present invention is to effectively eliminate misfolded protein aggregates, which cause degenerative brain diseases, by simultaneously activating p62 and autophagy.

The pharmacokinetics and key techniques of the present invention are summarized in FIG. 1.

Specifically, as shown in FIG. 1, major pathogenic proteins of proteinopathies such as mutant huntingtin and alpha-synuclein are converted to misfolded proteins which are insoluble in water, and then aggregated with each other and grow into oligomeric aggregates. These misfolded proteins grow further while acting as cytotoxic substances in neurons, and then grow into large oligomeric or fibrillar aggregates, eventually forming an inclusion body. In the above process, endoplasmic reticulum chaperones (①) such as BiP produce a large amount of Nt-Arg through N-terminal argination (②) by ATE1 R-transferase, and then the arginylated BiP (R-BiP) is translocated into the cytoplasm and binds to the misfolded huntingtin or alpha-synuclein (③). As a ligand, the Nt-Arg of R-BiP binds to the ZZ domain of p62. Due to the binding, the normally inactivated closed form of p62 is changed to an open form, leading to structural activation (④), and as a result, PB1 and LC3-binding domains are exposed. This activation results in the formation of oligomers and high molecular weight aggregates due to disulfide bonds of p62 (⑤), and increased binding to the autophagosome marker LC3 is finally delivered to autolysosome (⑥). In addition, p62 bound with N-terminal arginine migrates to the endoplasmic reticulum membrane and activates PI3P-mediated autophagosome biogenesis (⑦), thereby increasing intracellular autophagy (⑧).

p62 is a first-in-class target for autophagy activation proposed by the present inventors (FIG. 1, ⑧). In addition, no previous studies proposing p62 as a drug target for autophagy activation or the elimination of protein aggregates in degenerative brain diseases have been done.

Autophagy is a mechanism that acts to degrade or recycle cellular components that are unwanted or exhausted in cells, and in conditions such as nutrient and energy deficiencies, it can act for the production of energy and metabolites to be used in biosynthetic processes. The mechanism for autophagy is largely divided into macroautophagy, microautophagy and chaperone-mediated autophagy, and it is divided into bulk autophagy and selective autophagy, depending on the purpose of degrading the intracellular substrate. Of these, selective autophagy and chaperone-mediated autophagy cause selective degradation of unwanted intracellular proteins and dysfunctional organelles. By inducing selective autophagy, the development of new therapies for diseases based on the accumulation of misfolded proteins and dysfunctional organelles is currently building a new paradigm.

p62 protein is important for initiating the formation of autophagosome, which is a mediator in the mechanism for selective autophagy, and delivering the contents. It was observed that significant p62 activation of the novel p62 ligand according to the present invention induces p62 self-oligomerization. Further, in light of the fact that autophagosome targeting of p62 through this self-oligomerization is increased, this demonstrates that the novel p62 ligands according to the present invention can induce the targeting and degradation of p62 protein by intracellular autophagy. These results mean that the novel p62 ligand compounds according to the present invention can be utilized as more effective or supplemental alternative to existing anti-protein disease drugs.

PROTAC (PROteolysis Targeting Chimera) is a compound chimera of a ligand that recognizes a target protein and a ligand that recognizes an E3 ubiquitin enzyme. Since the paradigm of existing therapeutic agents for diseases is to inhibit protein enzymes, it is very important to develop a new therapeutic agent against protein-misfolding diseases that cannot be targeted with the existing therapeutic agent. From these viewpoints, PROTAC is an attractive new therapeutic development method by enabling selective degradation under ubiquitin-proteasome system with respect to proteins that cannot be targeted by a conventional enzyme inhibition method. However, currently, studies on PROTAC are limited only to the ubiquitin-proteasome system by utilizing only ligands that recognize the E3 ubiquitin enzyme, and thus has the folding problem associated with misfolded proteins in the aforementioned proteasome system. In contrast, since the novel p62 ligand according to the present invention can not only induce intracellular autophagy but also induce autophagosome targeting of cargo substrate proteins interacting with p62, it can provide a novel therapeutic agent that enables selective degradation under autophagy mechanisms of proteins that cannot be targeted by conventional enzyme inhibition methods.

The novel compound according to the present invention acts as a ligand binding to the ZZ domain of p62 protein, enhances the delivery of p62 to an autophagosome, activates autophagy, and eliminates misfolded protein aggregates, and therefore, is useful as a drug for preventing, ameliorating and treating various proteinopathies.

BRIEF DESCRIPTION OF THE DRAWINGS

FIG. 1 is a schematic diagram illustrating that the proteins arginylated by N-terminal rule binds to the p62 ZZ domain and degrades intracellular substances such as proteins through intracellular autophagy activity.

FIG. 2 is an immunoblot assay result showing the effect of increasing the p62 protein oligomerization activity of p62 ligand compounds (YOK-1104, YOK-2204, YOK-3304, YOK-1204, YOK-4404, YOK-1107, YOK-1109, YOK-2207, YOK-2209, YT-4-1, YT-4-2, YT-6-1, YT-6-2, YT-6-7, YT-6-8, YT-9-1 and YT-9-2) according to the present invention.

FIG. 3 is an immunoblot assay result showing the effect of increasing the autophagy activity of p62 ligand compounds (YOK-1107, YOK-4404, 3301, 3302 and YOK-1104) according to the present invention.

FIG. 4 is an immunoblot assay result showing the effect of increasing the autophagy activity of p62 ligand compounds (YOK-1106, YOK-1107, YOK-1204, YOK-1304, YOK-2204, YOK-4404) according to the present invention.

FIG. 5 is an immunoblot assay result confirming that control compounds (1101, 1102, 1103, 1201, 1202, 1203, 1301, 1302, YTK-1105-1, 4402, 1401, 1402, 2201 and 2202) do not increase autophagy activity.

FIGS. 6a and 6b are immunofluorescence staining assay results confirming that the p62 ligand compounds (YOK-1106, YOK-1204, YOK-1504, YOK-2204, YOK-3304 and YOK-4404) according of the present invention allow the activation and oligomerization of p62 proteins, and then show the efficacy of delivering them to autophagosome and simultaneously increasing autophagy activity.

FIG. 7 is immunofluorescence staining assay results confirming that the control compounds (YOK-A-1104, YOK-G-1104, YTK-1005 and YTK-1105-1) allow the activation and oligomerization of p62 proteins and then show the efficacy of delivering them to autophagosome and simultaneously increasing autophagy activity.

FIGS. 8a and 8b, and FIGS. 9a and 9b are immunofluorescence staining assay results showing the efficacy of delivering target proteins to autophagy. This is the result showing that after treatment with the compounds, markers of target proteins, FK2 (FIGS. 8a and 8b) or HuntingtinQ103-GFP (FIGS. 9a and 9b), gradually increase in terms of the co-existence of p62 protein with intracellular puncta.

DETAILED DESCRIPTION OF THE EMBODIMENTS

Hereinafter, the present invention will be described in more detail.

The definition of groups used herein are described in detail. Unless otherwise indicated, each group has the following definition.

As used herein, the term "halo" includes fluoro, chloro, bromo and iodo.

As used herein, the "alkyl" refers to a linear or branched aliphatic hydrocarbon radical, and may be preferably an alkyl having 1 to 6 carbon atoms, more preferably an alkyl having 1 to 4 carbon atoms. Examples of such alkyl include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In one aspect of the invention, there is provided a compound represented by the following Chemical Formula 1, a pharmaceutically acceptable salt, stereoisomer, hydrate, solvate or prodrug thereof:

[Chemical Formula 1]

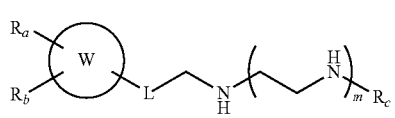

in Chemical Formula 1,

W is C6-C10 aryl;

L is —O—(CH$_2$)$_{n1}$—CH(OH)—, provided that O in the —O—(CH$_2$)$_{n1}$—CH(OH)— is bonded to a benzene ring, where n1 is an integer of 1 to 4;

m is an integer of 0 to 2;

$R_a$ is $R_1$ or —$OR_1$, where $R_1$ is hydrogen or —$(CH_2)_{n2}$—$R'_1$, $R'_1$ is phenyl which is unsubstituted or substituted by hydroxy, halogen, $C_{1-4}$ alkyl, $C_{1-4}$ alkoxy, nitro, amino, ($C_{1-4}$ alkyl)amino, or di($C_{1-4}$ alkyl)amino, n2 is an integer of 1 to 6;

$R_b$ is —$OR_2$, where $R_2$ is hydrogen or —$(CH_2)_{n3}$—$R'_2$, $R'_2$ is phenyl which is unsubstituted or substituted by hydroxy, halogen, $C_{1-4}$ alkyl, $C_{1-4}$ alkoxy, nitro, amino, ($C_{1-4}$ alkyl)amino, or di($C_{1-4}$ alkyl)amino, n3 is an integer of 1 to 6;

$R_c$ is —$(CH_2)_{n4}$—OH, —$(CH_2)_{n4}$—NH—C(=NH) $NH_2$, —C(=NH) $NH_2$, $C_{1-6}$ alkyl, —CH($R_3$)—COO—$R_4$, or —CH(COO—$R_4$)—$CH_2CH_2CH_2$—NH—C(=NH) $NH_2$, —$(CH_2)_{n4}$—O—$(CH_2)_{n4}$—$OR_4$, —CONH$(CH_2)_{n4}$—$OR_4$, —CO$(CH_2)_{n5}$—$OR_4$, —$(CH_2)_{n5}$—CH($NH_2$)—$COOR_4$, —$(CH_2)_{n5}$—$CONHR_4$, n4 is an integer of 2 to 4, n5 is an integer of 1 to 4, $R_3$ is hydrogen or $C_{1-4}$ alkyl, and $R_4$ is hydrogen, or $C_{1-4}$ alkyl.

Preferably, the W may be phenyl.

Preferably, the n1 may be 1 or 2.

Preferably, the $R_a$ may be hydrogen or —O—$(CH_2)_{n2}$—$R'_1$.

Preferably, the $R'_1$ may be phenyl that is unsubstituted or substituted by hydroxy, fluoro, chloro, bromo, methyl, ethyl, methoxy, ethoxy, nitro, amino or dimethylamino.

Preferably, the n2 may be an integer of 1 to 4.

Preferably, the $R_b$ may be hydroxy, or —O—$(CH_2)_{n3}$—$R'_2$.

Preferably, the $R'_2$ may be phenyl which is unsubstituted or substituted by hydroxy, fluoro, chloro, bromo, methyl, ethyl, methoxy, ethoxy, nitro, amino or dimethylamino.

Preferably, the n3 may be an integer of 1 to 4.

Preferably, the $R_c$ may be —$(CH_2)_{n4}$—OH, —$(CH_2)_{n4}$—NH—C(=NH)$NH_2$, —C(=NH)$NH_2$, methyl, ethyl or isopropyl.

Preferably, the n4 may be an integer of 2 to 3.

Preferably, the n5 may be an integer of 1 to 3.

Preferably, the $R_4$ may be hydrogen or methyl.

Specifically, representative examples of the compound represented by Chemical Formula 1 are as follows:

1) (R)-1-(3,4-(bis(benzyloxy)phenoxy)-3-((2-hydroxyethyl)amino)propan-2-ol (YOK-1106);
2) (R)-1-(3,4-(bis((4-chlorobenzyl)oxy)phenoxy)-3-((2-hydroxyethyl)amino)propan-2-ol (YT-6-1);
3) (R)-1-(3-((4-chlorobenzyl)oxy)phenoxy)-3-((2-hydroxyethyl)amino)propan-2-ol (YT-6-2);
4) (R)-1-(3-((4-chlorobenzyl)oxy)phenoxy)-3-((2-hydroxyethyl)amino)propan-2-ol (YT-6-7);
5) (R)-1-(3-((4-fluorobenzyl)oxy)phenoxy)-3-((2-hydroxyethyl)amino)propan-2-ol (YT-6-8);
6) (R)-1-(2-((3-(3,4-bis(benzyloxy)phenoxy)-2-hydroxypropyl)amino)ethyl)guanidine (YOK-1109);
7) (R)-1-(2-((3-(3,4-diphenethoxyphenoxy)-2-hydroxypropyl)amino)ethyl)guanidine (YOK-2209);
8) (R)-1-(2-((3-(3,4-bis(4-chlorobenzyl)oxy)phenoxy)-2-hydroxypropyl)amino)ethyl)guanidine (YT-9-1);
9) (R)-1-(2-((3-(3,4-bis(4-fluorobenzyl)oxy)phenoxy)-2-hydroxypropyl)amino)ethyl)guanidine (YT-9-2);
10) (R)-1-(3-(3,4-bis(benzyloxy)phenoxy)-2-hydroxypropyl)guanidine (YOK-1107);
11) (R)-1-(3-(3,4-diphenethoxyphenoxy)-2-hydroxypropyl)guanidine (YOK-2207);
12) (R)-1-(3,4-bis(benzyloxy)phenoxy)-3-(isopropylamino)propan-2-ol (YOK-1104);
13) (R)-1-(3,4-diphenethoxyphenoxy)-3-(isopropylamino)propan-2-ol (YOK-2204);
14) (R)-1-(3,4-bis(3-phenylpropoxy)phenoxy)-3-(isopropylamino)propan-2-ol (YOK-3304);
15) (R)-1-(3,4-bis(4-phenylbutoxy)phenoxy)-3-(isopropylamino)propan-2-ol (YOK-4404);
16) (R)-1-(4-(benzyloxy)-3-phenethoxyphenoxy)-3-(isopropylamino)propan-2-ol (YOK-1204);
17) (R)-1-(4-(benzyloxy)-3-(3-phenylpropoxy)phenoxy)-3-(isopropylamino)propan-2-ol (YOK-1304);
18) (R)-1-(3,4-bis((4-chlorobenzyl)oxy)phenoxy)-3-(isopropylamino)propan-2-ol (YT-4-1); and
19) (R)-1-(3,4-bis((4-fluorobenzyl)oxy)phenoxy)-3-(isopropylamino)propan-2-ol (YT-4-2).

Meanwhile, the compounds of the present invention may exist in the form of a pharmaceutically acceptable salt. As the salt, an addition salt formed by pharmaceutically acceptable free acids may be useful. The term "pharmaceutically acceptable salt" used herein refers to any organic or inorganic addition salt of the compounds represented by Chemical Formulae 1 to 3, in which the adverse effect caused by the salt does not impair the beneficial effect of the compounds at a concentration exhibiting relatively non-toxic and non-harmful effective activity to a patient.

The acid addition salt may be prepared by a common method, for example, by dissolving a compound in an excess amount of aqueous acid solution and precipitating the resulting salt using a water-miscible organic solvent, such as methanol, ethanol, acetone or acetonitrile. Alternatively, an equimolar amount of a compound and an acid in water or alcohol (e.g., glycol monomethyl ether) can be heated, and subsequently, the resulting mixture can be dried by evaporating, or precipitated salts can be filtered under suction.

In this case, the free acid may be an inorganic acid or an organic acid. Examples of the inorganic acids include, but are not limited to, hydrochloric acid, phosphoric acid, sulfuric acid, nitric acid and stannic acid. Examples of the organic acids include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering the undissolved compound salt, and then evaporating the filtrate until dry. At this time, as the metal salts, particularly sodium, potassium or calcium salts are pharmaceutically suitable, but the present invention is not limited thereto. Also, the corresponding silver salts may be obtained by reacting an alkali metal or alkaline earth metal salt with a proper silver salt (e.g., silver nitrate).

Pharmaceutically acceptable salts of the compound of the present invention, unless otherwise indicated herein, include salts of acidic or basic groups, which may be present in the compound of Chemical Formula 1. For example, the pharmaceutically acceptable salts include sodium, calcium and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate). The salts may be prepared using a salt preparation method known in the art.

Salts of the compounds of Chemical Formula 1 of the present invention are pharmaceutically acceptable salts, and can be used without particular limitation as long as they are salts of the compounds of Chemical Formula 1 which can exhibit pharmacological activities equivalent to those of the compound of Chemical Formula 1, for example, can prevent or treat neurodegenerative diseases by inducing autophagic degradation of intracellular neurodegenerative disease and tumor-associated proteins through a ligand of p62.

In addition, the compounds represented by Chemical Formula 1 according to the present invention include, but are not limited thereto, not only pharmaceutically acceptable salts thereof, but also all solvates or hydrates and all possible stereoisomers that can be prepared therefrom. All stereoisomers of the present compounds (e.g., those which may exist due to asymmetric carbons on various substituents), including enantiomeric forms and diastereomeric forms, are contemplated within the scope of this invention. Individual stereoisomers of the compounds of the present invention may, for example, be substantially free of other isomers (e.g., as a pure or substantially pure optical isomer having a specified activity), or may be admixed, for example, as racemates or with all other, or other selected, stereoisomers. The chiral centers of the compounds of the present invention may have the S or R configuration as defined by the IUPAC 1974 Recommendations. The racemic forms can be analyzed by physical methods, such as fractional crystallization, separation or crystallization of diastereomeric derivatives or separation by chiral column chromatography. The individual optical isomers can be obtained from the racemates by any suitable method, including without limitation, salt formation with an optically active acid followed by crystallization.

The solvate and stereoisomer of the compound represented by Chemical Formula 1 may be prepared from the compound represented by Chemical Formula 1 using methods known in the art.

Furthermore, the compound represented by Chemical Formula 1 according to the present invention may be prepared either in a crystalline form or in a non-crystalline form, When the compound is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

The compound of Chemical Formula 1 according to the present invention may be prepared by the same method as in Reaction Schemes 1 to 5, which are the following exemplary methods, and specific examples thereof are the same as those described in the following Examples.

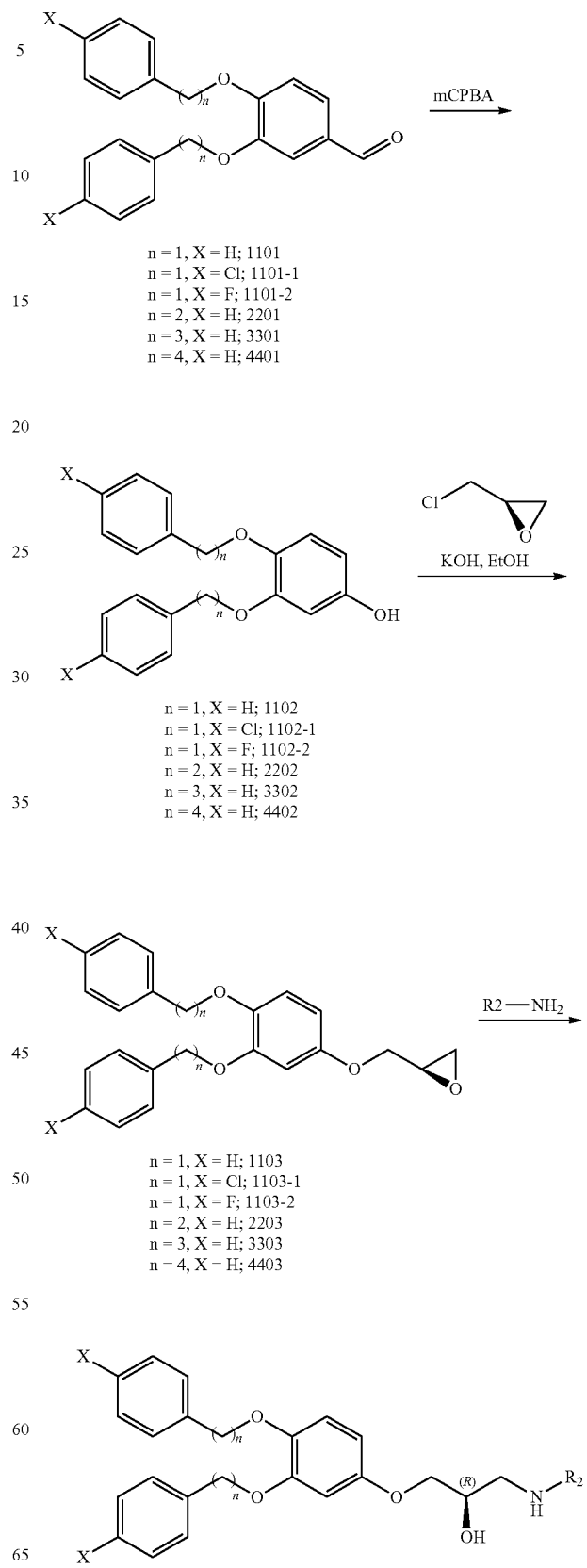

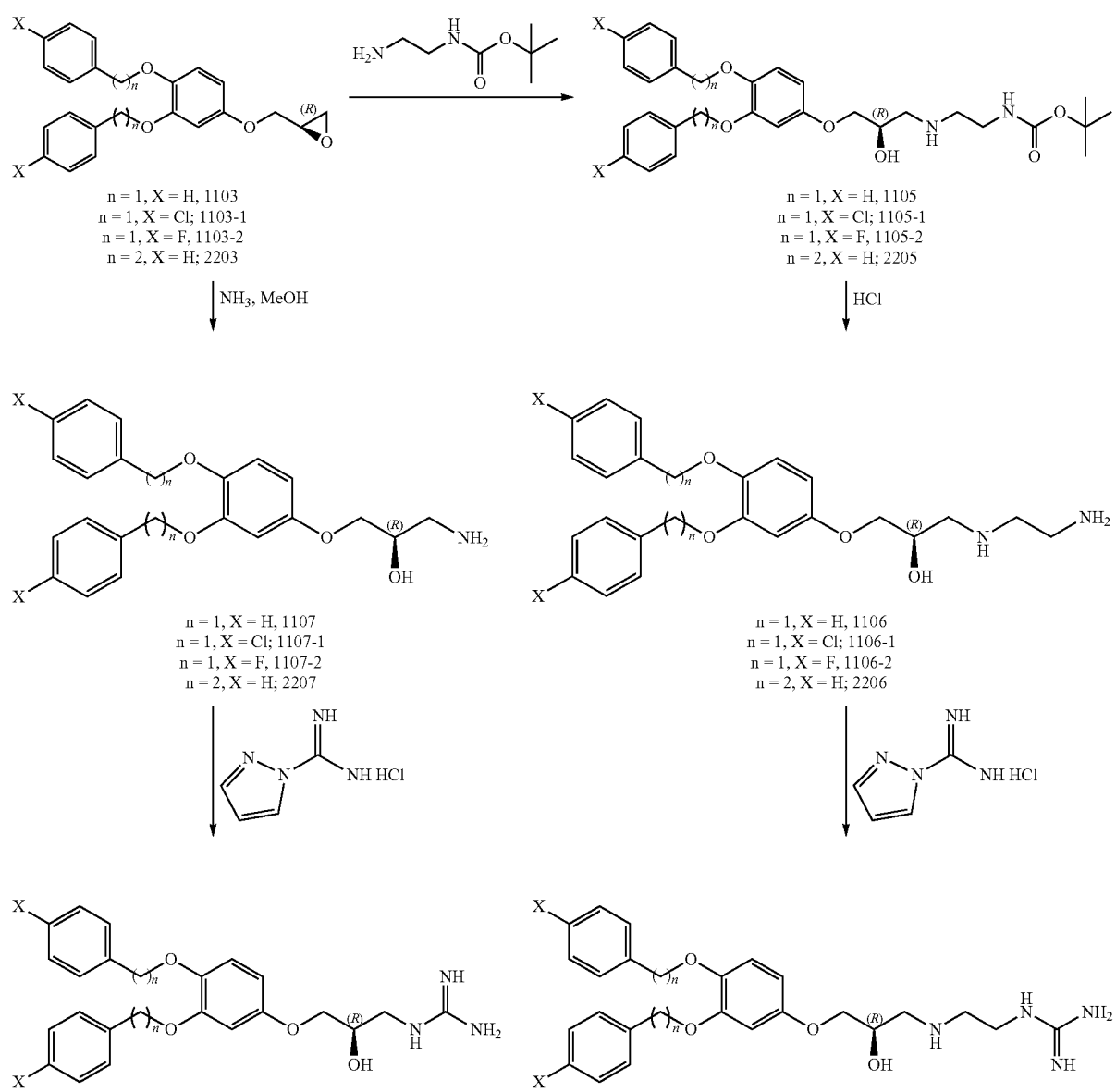
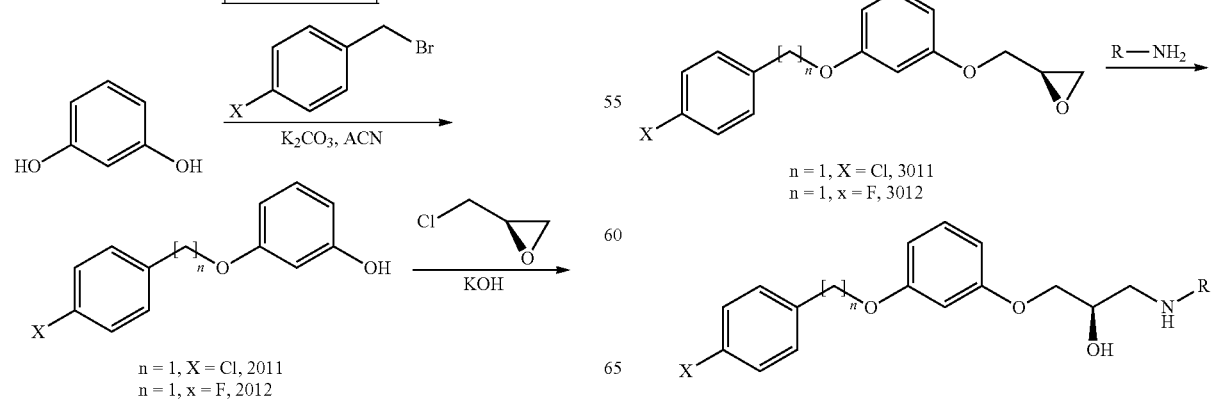

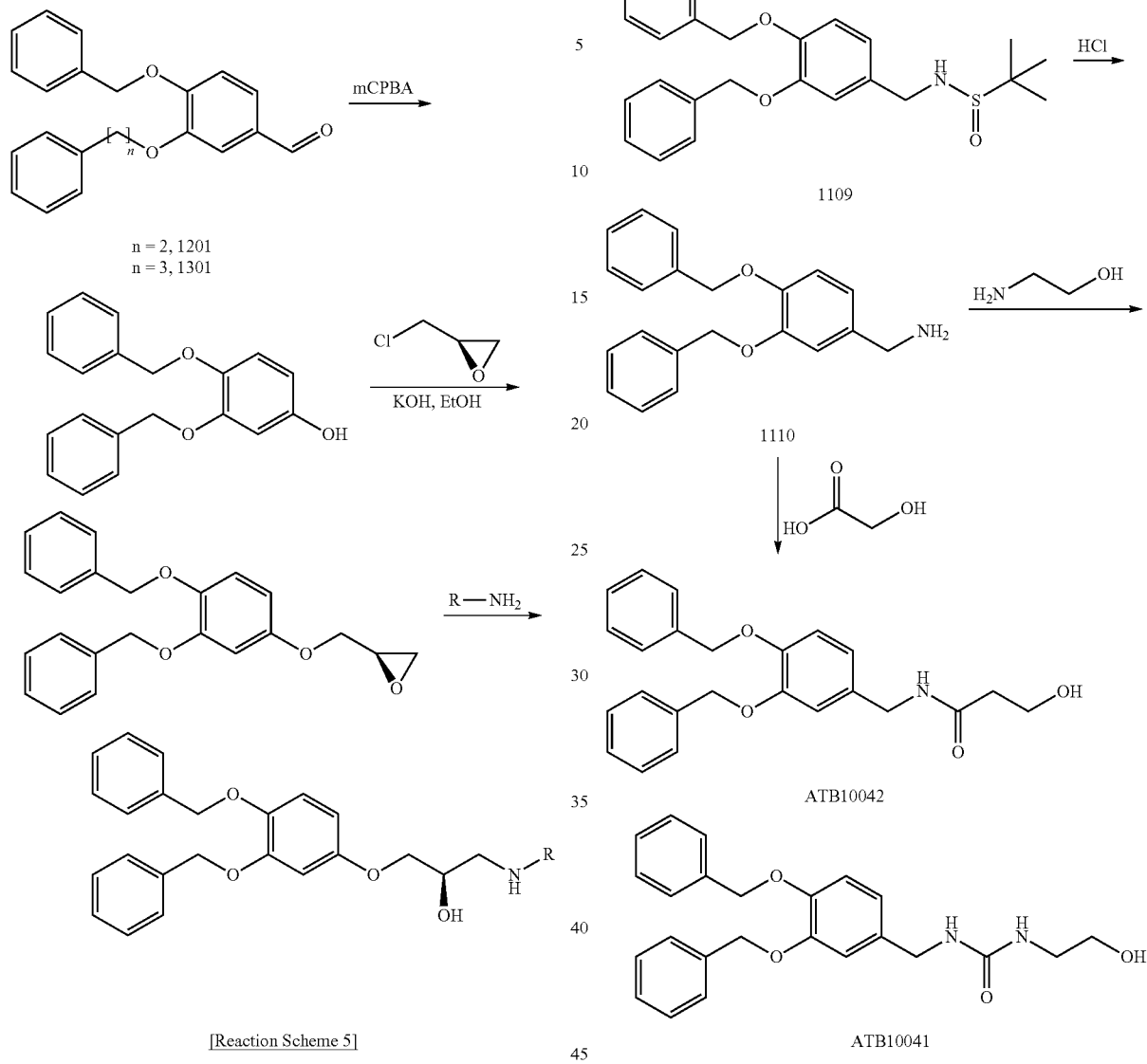
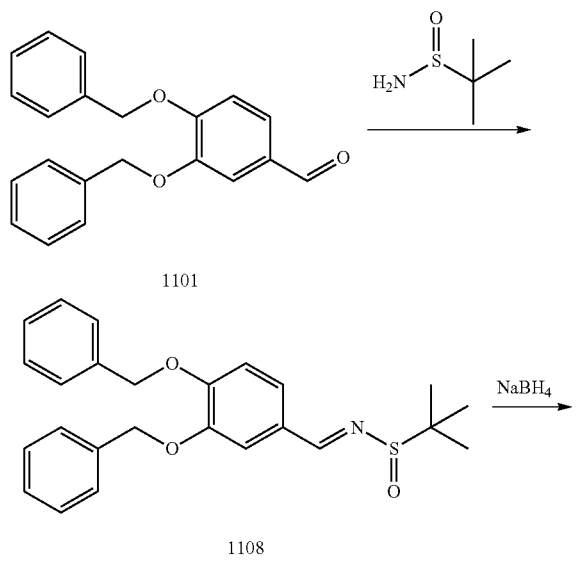

In the preparation method of the present invention, the reactants used in Reaction Schemes may be commercially available compounds, or may be synthesized by performing one or more reactions known in the art as they are or by appropriately modifying the reactions. For example, in consideration of the presence, type and/or position of reactive functional groups and/or hetero elements contained in the skeletal structure, the reactants may be synthesized by performing one or more reactions in a series of order, but are not limited thereto.

The compound of Chemical Formula 1 according to the present invention is characterized by functioning as a ligand that binds to the ZZ domain of p62 and thus activating the function of p62. By activating the function of p62, the compound of Chemical Formula according to the present invention can activate autophagy.

Therefore, in another aspect, the present invention provides a pharmaceutical composition for autophagy activation comprising a compound of Chemical Formula 1, a pharmaceutically acceptable salt, stereoisomer, hydrate, solvate or prodrug thereof.

The compound of Chemical Formula 1 according to the present invention can eliminate aggregated proteins linked to misfolded protein aggregation-related diseases due to the activating action of autophagy. In addition, the compound of Chemical Formula 1 is a p62 ligand, which binds to the p62 ZZ domain and activates PB1 domain and LIR domain of p62 protein, so that it induces p62 oligomerization and aggregate formation and also increases autophagosome formation by inducing p62 aggregate formation. By the processes above, misfolded proteins can be efficiently eliminated (see FIG. 1). Such protein may be a major protein of proteinopathies, more preferably at least one selected from the group consisting of prion protein, amyloid precursor protein (APP), alpha-synuclein, superoxide dismutase 1, tau, immunoglobulin, amyloid-A, transthyretin, beta2-microglobulin, cystatin C, apolipoprotein A1, TDP-43, islet amyloid polypeptide, ANF, gelsolin, insulin, lysozyme, fibrinogen, huntingtin, alpha-1-antitrypsin Z, crystallin, c9 open reading frame 72 (c9orf72), glial fibrillary acidic protein, cystic fibrosis transmembrane conductance regulator protein, rhodopsin, and ataxin, and other proteins with a poly-Q stretch.

Therefore, in still another aspect, the present invention provides a pharmaceutical composition for the prevention, amelioration or treatment of proteinopathies comprising a p62 ligand compound of Chemical Formula 1, a pharmaceutically acceptable salt, stereoisomer, hydrate, solvate or prodrug thereof.

The term "aggregation", in accordance with the present invention, refers to the formation of oligomeric or multimeric complexes of typically one or more types of proteins, which may be accompanied by the integration of additional biomolecules, like carbohydrates, nucleic acids and lipids, into the complexes. Such aggregated proteins may form deposits in specific tissue, more preferably in nerve tissue or tissue of the brain. The extent of aggregation depends on the particular disease.

The term "proteinopathy" or "disease linked to protein aggregation" as used herein, refers to those diseases which are characterized by the presence of aggregated proteins, Examples thereof include, but are not limited to, neurodegenerative diseases, alpha-1 antitrypsin deficiency, keratopathy, retinitis pigmentosa, type 2 diabetes, cystic fibrosis, and the like.

The neurodegenerative diseases herein are preferably selected from the group consisting of Lyme borreliosis, fatal familial insomnia, Creutzfeldt-Jakob Disease (CJD), multiple sclerosis (MS), dementia, Alzheimer's disease, epilepsy, Parkinson's disease, stroke, Huntington's disease, Picks disease, amyotrophic lateral sclerosis (ALS), spinocerebellar ataxias, other Poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

The dosage of the pharmaceutical composition of the present invention may vary with a broad range depending on weight, age, gender, or health condition a patient, diet, administration period, administration method, excretion and severity of disease. However, the effective dosage is generally about 1 ng to 10 mg/day and particularly about 1 ng to 1 mg/day for an adult (60 kg). As the dosage may vary depending on various conditions, it would be evident to a person skilled in the pertinent art that the dosage may be increased or decreased. Accordingly, the scope of the present invention is not limited by the aforementioned dosage in any way. As for the number of administration, the administration can be made either once or several divided times per day within a desired range, and the administration period is not particularly limited, either.

As used herein, the term "treatment" refers to all actions that alleviate or beneficially change the symptoms of various diseases linked to misfolded protein aggregation, such as proteinopathies by administering the pharmaceutical composition of the present invention.

As described above, the compound of the present invention exhibits the effects of (1) inducing p62 oligomerization and structural activation, (2) increasing p62-LC3 binding, and (3) increasing the delivery of p62 to autophagosomes, (4) activating autophagy, and finally (5) eliminating misfolded protein aggregates. Therefore, the pharmaceutical composition containing this compound as an active ingredient can be used for the prevention, amelioration or treatment of diseases linked to various misfolded protein aggregation.

For example, the composition of the present invention may further include pharmaceutically acceptable carriers, diluents or excipients. The composition can be used in the various forms such as oral dosage forms of powders, granules, tablets, capsules, suspensions, emulsions, syrups, aerosols and injections of a sterile injectable solution, which are formulated by the conventional method according to the purpose of each of the intended use. The composition can be administered through various routes including oral administration or intravenous, intraperitoneal, subcutaneous, rectal and topical administration. Examples of suitable carriers, excipients or diluents which can be included in this composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxy benzoate, propylhydroxy benzoate, talc, magnesium stearate, mineral oil, and the like. In addition, the composition of the present invention may further include fillers, anti-coagulants, lubricants, humectants, fragrances, emulsifiers, preservatives, and the like.

A solid formulation for oral administration includes tablets, pills, powders, granules, capsules and the like, and such solid dosage forms are formulated by mixing the composition of the present invention with one or more excipients, such as starch, calcium carbonate, sucrose, lactose, gelatin and the like. Also, lubricants such as magnesium stearate and talc can be used in addition to simple excipients.

A liquid formulation for oral administration can be illustrated as suspensions, solutions, emulsions, syrups and the like, and can include various excipients such as humectants, sweeteners, fragrances, preservatives and the like, in addition to water and liquid paraffin which are commonly used diluents.

A formulation for parenteral administration includes sterilized aqueous solutions, non-aqueous solvents, suspension agents, emulsion agents, lyophilizing agents and suppository agents. Non-aqueous solvent and suspending agent may include propylene glycol, polyethylene glycol, vegetable oil such as olive oil, and injectable esters such as ethyl oleate. As a substrate for the suppository agent, Witepsol, Macrogol, Tween 61, cacao butter, laurin butter, glycerogelatin or the like may be used. On the other hand, injections may include conventional additives such as solubilizing agents, isotonic agents, suspending agents, emulsifiers, stabilizers, or preservatives.

The formulation may be prepared according to conventional mixing, granulation or coating methods, and contains an active ingredient in an amount effective for medical treatment, specifically for the prevention, amelioration or treatment of diseases linked to misfolded protein aggregation.

In this case, the composition of the present invention is administrated in a pharmaceutically effective amount. The term "pharmaceutically effective amount" as used herein refers to an amount which is sufficient to treat the disease at a reasonable benefit/risk ratio applicable for any medical treatment, and also which is enough to not cause side effects. The level of effective amount can be determined depending on patient's health condition, disease type, severity of the disease, activity of the drug, sensitivity on the drug, administration method, administration time, administration route, excretion rate, treatment duration, combination, factors including other medicines used at the same time and other factors well-known in the medical field. The composition of the present invention may be administered as individual therapy or in combination with other therapies, and it can be administered simultaneously with or sequentially to conventional therapies, and once or multiple times. It is important to administer the minimum amount which can provide the maximum effect without the side effects in consideration of all the above factors, which can be easily determined by those skilled in the art.

For example, the dosage may be increased or decreased depending on administration route, the severity of a disease, gender, weight, age and the like, and the scope of the present invention is not limited by the aforementioned dosage in any way.

A preferred dose of the compound according to the present invention may be varied according to the condition and weight of a patient, the severity of a disease, the type of a drug, and the route and duration of administration, but it may be suitably selected by those skilled in the art.

In still another aspect, the present invention provides a method for preventing, ameliorating or treating diseases linked to the aggregation of misfolded proteins, comprising administering the pharmaceutical composition of the present invention to a subject in need thereof.

As used herein, the term "subject" refers to all animals comprising human, monkey, cow, horse, sheep, pig, chicken, turkey, quail, cat, dog, mouse, rat, rabbit, or guinea pig, which have diseases linked to misfolded protein aggregation. The diseases linked to misfolded protein aggregation can be effectively prevented, ameliorated or treated by administrating the pharmaceutical composition of the present invention to the subject. In addition, since the pharmaceutical composition of the present invention functions as a p62 ligand to activate autophagy, eliminates aggregates of misfolded proteins due to the autophagy activation, and thus exhibits a prophylactic or therapeutic effect of diseases linked to these aggregated proteins, it can exhibit synergistic effects by administration in combination with existing therapeutic agents.

As used herein, the term "administration" means introduction of a prescribed amount of a substance into a patient in certain appropriate method, and the composition of the present invention can be administrated via any of the general routes as long as it can reach a target tissue. For example, intraperitoneal administration, intravenous administration, intramuscular administration, subcutaneous administration, intradermal administration, oral administration, topical administration, intranasal administration, intrapulmonary administration and intrarectal administration may be performed, but the present invention is not limited to these exemplified administration modes. Also, the pharmaceutical composition of the present invention can be administered using any device capable of delivering the active ingredients to target cells. Preferable administration mode and formulation are an intravenous injection, a subcutaneous injection, an intradermal injection, an intramuscular injection, intravenous drip injection, or the like. Injectable formulations may be prepared using saline, aqueous solutions such as Ringer's solution, and non-aqueous solutions, such as vegetable oils, high fatty acid esters (e.g., ethyl oleic acid, etc.), alcohols (e.g., ethanol, benzyl alcohol, propylene glycol, glycerin, etc.). The injectable preparations may include pharmaceutical carriers, including a stabilizer for preventing degeneration (e.g., ascorbic acid, sodium hydrogen sulfite, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzylalcohol, etc.).

In the other aspect, the present invention provides a food composition for the prevention or amelioration of misfolded protein-associated diseases comprising a p62 ligand compound of Chemical Formula 1, a pharmaceutically acceptable salt, stereoisomer, hydrate, solvate or prodrug thereof. The food composition is a health functional food and it can be used through formulation itself or be comprised in other health functional foods as an additive of health functional food. The health functional food means food having body modulating function such as prevention or amelioration of diseases, biodefense, immunity, recovery of convalescence, aging inhibition, etc., and it should be harmless to human body when taking in a long term. The mixing amount of active ingredients can be properly decided depending on purpose of use (prevention, health or therapeutic treatment).

The kind of the food is not particularly limited. Examples of food where the above substances can be added are meat, sausage, bread, chocolates, candies, snack, cookies, pizza, ramen, other noodles, gum, dairy products including ice cream, sorts of soup, beverages, tea, drinks, alcohol beverages and vitamin complex, etc., and it includes all the health functional foods in the common sense.

The food composition of the present invention can comprise common ingredients used in preparation of food or food additives, specifically, a flavoring agent; a natural sweetener such as monosaccharides like glucose, fructose, disaccharides like maltose, sucrose, and dextrin, cyclodextrin as a natural carbohydrate, or a synthetic sweetener such as saccharin, aspartame; a nutrient; vitamin; electrolyte; a coloring agent; an organic acid; a protective colloid viscosity agent; pH regulator; a stabilizer; a preservative; glycerin; alcohol; a carbonating agent which is used on carbonated drinks, etc.

In a specific embodiment of the present invention, the compounds of Examples 1 to 19, which are novel p62 ligands represented by Chemical Formula 1, were newly synthesized. In addition, in order to evaluate whether the novel p62 ligand compounds according to the present invention can increase the phenomenon of autophagy in cultured cells, HeLa cell lines, which are cell lines derived from cervical cancer patients, were treated with the novel p62 ligand compound according to the present invention and cultured, and then autophagy activity in cultured cells was confirmed by immunoblotting. As a result, it was confirmed that the level of LC3, which is a marker of autophagy activity, increased gradually according to the time of treatment with the p62 ligand compounds of the present invention, and that the p62 ligand compounds according to the present invention activated and oligomerized p62 proteins and delivered to autophagosome and simultaneously increased autophagy activity, thereby effectively eliminating misfolded protein aggregates.

EXAMPLE

Hereinafter, the present invention will be described in more detail with reference to Examples. However, these Examples are provided for illustrative purposes only, and the present invention is not intended to be limited by these Examples.

The compounds shown in Table 1 below were prepared by the methods according to the following Examples 1 to 19.

TABLE 1

| Example | Code No. | Compound Name |
|---|---|---|
| 1 | YOK-1106 | (R)-1-(3,4-(bis(benzyloxy)phenoxy)-3-((2-hydroxyethyl)amino)propan-2-ol |
| 2 | YT-6-1 | (R)-1-(3,4-(bis((4-chlorobenzyl)oxy)phenoxy)-3-((2-hydroxyethyl)amino)propan-2-ol |
| 3 | YT-6-2 | (R)-1-(3,4-(bis((4-fluorobenzyl)oxy)phenoxy)-3-((2-hydroxyethyl)amino)propan-2-ol |
| 4 | YT-6-7 | (R)-1-(3-((4-chlorobenzyl)oxy)phenoxy)-3-((2-hydroxyethyl)amino)propan-2-ol |
| 5 | YT-6-8 | (R)-1-(3-((4-fluorobenzyl)oxy)phenoxy)-3-((2-hydroxyethyl)amino)propan-2-ol |
| 6 | YOK-1109 | (R)-1-(2-((3-(3,4-bis(benzyloxy)phenoxy)-2-hydroxypropyl)amino)ethyl)guanidine |
| 7 | YOK-2209 | (R)-1-(2-((3-(3,4-diphenethoxyphenoxy)-2-hydroxypropyl)amino)ethyl)guanidine |
| 8 | YT-9-1 | (R)-1-(2-((3-(3,4-bis(4-chlorobenzyl)oxy)phenoxy)-2-hydroxypropyl)amino)ethyl)guanidine |
| 9 | YT-9-2 | (R)-1-(2-((3-(3,4-bis(4-fluorobenzyl)oxy)phenoxy)-2-hydroxypropyl)amino)ethyl)guanidine |
| 10 | YOK-1107 | (R)-1-(3-(3,4-bis(benzyloxy)phenoxy)-2-hydroxypropyl)guanidine |
| 11 | YOK-2207 | (R)-1-(3-(3,4-diphenethoxyphenoxy)-2-hydroxypropyl)guanidine |
| 12 | YOK-1104 | (R)-1-(3,4-bis(benzyloxy)phenoxy)-3-(isopropylamino)propan-2-ol |
| 13 | YOK-2204 | (R)-1-(3,4-diphenethoxyphenoxy)-3-(isopropylamino)propan-2-ol |
| 14 | YOK-3304 | (R)-1-(3,4-bis(3-phenylpropoxy)phenoxy)-3-(isopropylamino)propan-2-ol |
| 15 | YOK-4404 | (R)-1-(3,4-bis(4-phenylbutoxy)phenoxy)-3-(isopropylamino)propan-2-ol |
| 16 | YOK-1204 | (R)-1-(4-(benzyloxy)-3-phenethoxyphenoxy)-3-(isopropylamino)propan-2-ol |
| 17 | YOK-1304 | (R)-1-(4-(benzyloxy)-3-(3-phenylpropoxy)phenoxy)-3-(isopropylamino)propan-2-ol |
| 18 | YT-4-1 | (R)-1-(3,4-bis((4-chlorobenzyl)oxy)phenoxy)-3-(isopropylamino)propan-2-ol |
| 19 | YT-4-2 | (R)-1-(3,4-bis((4-fluorobenzyl)oxy)phenoxy)-3-(isopropylamino)propan-2-ol |

In the case of the starting materials for synthesizing the compounds of the present invention, various synthesis methods have been known, and if available on the market, the starting materials may be purchased from the providers. Examples of the reagents suppliers include Sigma-Aldrich, TCI, Wako, Kanto, Fluorchem, Acros, Alfa, Fluka, and the like, but are not limited thereto.

The compounds of the present invention can be prepared from readily available starting materials using the following general methods and procedures. As for typical or preferred process conditions (i.e., reaction temperature, time, molar ratio of reactants, solvents, pressure) and the like, other process conditions may also be used unless stated otherwise. The optimal reaction state may vary depending on the specific reactants or solvent used. Such conditions can be determined by one skilled in the art by conventional optimization procedures.

Hereinafter, the preparation methods of Examples to 19 are described.

Preparation Example 1) Compounds of Examples 1, 2, 3, 12, 13, 14, 15, 18 and 19 were synthesized by the method shown in Reaction Scheme 1 below.

[Reaction Scheme 1]

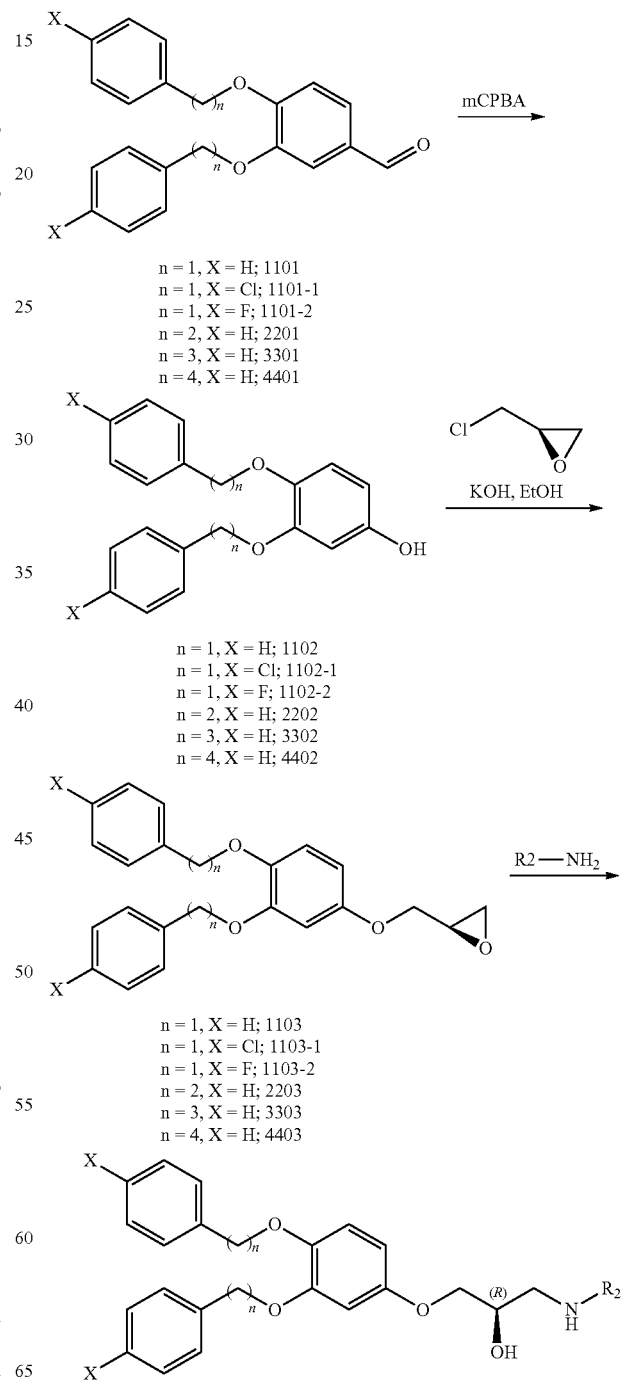

Example 1: Preparation of (R)-1-(3,4-(bis(benzyloxy)phenoxy)-3-((2-hydroxyethyl)amino)propan-2-ol (YOK-1106)

Step 1) Preparation of 3,4-bis(benzyloxy)phenol (1102)

After dichloromethane (15 ml) was added to and dissolved in 3,4-bis(benzyloxy)benzaldehyde (1101, 1.00 g, 3.0 mmol, 1 eq.), mCPBA (0.78 g, 4.5 mmol, 1.5 eq.) was added to the reaction and stirred at room temperature for 4 hours. The reaction mixture was diluted with ethyl acetate, and washed with a saturated aqueous sodium carbonate solution, and the organic layer was separated. The organic layer was washed with an aqueous sodium chloride solution, then dehydrated with anhydrous sodium sulfate and filtered under reduced pressure. The filtered solution was concentrated and then dissolved again in methanol (10 ml), and 6N NaOH was added and stirred at room temperature for 30 minutes. 4N HCl solution was added to the reaction, and further stirred for 30 minutes. The reaction mixture was diluted with ethyl acetate (50 ml), washed with brine, and then dehydrated with anhydrous sodium sulfate, and filtrated under reduced pressure. The filtered solution was concentrated and then purified by column chromatography (hexane/ethyl acetate ratio=7/3) to give 3,4-bis(benzyloxy)phenol (1102, 0.87 g, yield: 90%).

$^1$H-NMR (CDCl$_3$, 300 MHz): δ 7.25-7.42 (m, 10H), 6.80 (d, 1H, J=9.0 Hz), 6.48 (d, 1H, J=3.0 Hz), 6.29 (dd, 1H, J=3.0 and 9.0 Hz), 5.08 (d, 4H, J=Hz), 4.55 (s, 1H); ESIMS m/z: 307.25 [M+H]$^+$.

Step 2) Preparation of R-2-((3,4-bis(benzyloxy)phenoxy)methyl)oxirane (1103)

3,4-Dibenzyloxyphenol (1102, 306 mg, 1.0 mmol) was diluted with ethanol (10 ml), and then KOH aqueous solution (KOH 66 mg, 1.2 mmol, 1 ml) and (R)-2-(chloromethyl)oxilrane (410 ul, 5.0 mmol) were added sequentially. The reaction mixture was stirred at room temperature or 5 hours, and then the organic solvent was removed under reduced pressure. The concentrated reaction mixture was diluted again with ethyl acetate, washed with water and then washed with brine. The extracted organic layer was dehydrated with anhydrous sodium sulfate and then filtered under reduced pressure. The filtered organic layer was concentrated and purified by column chromatography to give pure R-2-((3,4-bis(benzyloxy)phenoxy)methyl)oxirane (1103, 297 mg, yield: 82%). ESIMS m/z: 363.5 [M+H]$^+$.

Step 3) R-2-((3,4-bis(benzyloxy)phenoxy)methyl)oxirane (1103, 9 mg, 25 nmol) was diluted with anhydrous ethanol (1 ml), and then 2-aminoethan-1-ol (7.6 μL, 125 nmol) was added thereto and stirred at room temperature for 4 hours. After confirming the reaction by TLC, the reaction solvent was concentrated under reduced pressure, water was added to the concentrated reaction product, and extracted with dichloromethane (3×5 mL). The extracted organic layer was dehydrated with anhydrous sodium sulfate and then filtered under reduced pressure. The filtered organic layer was concentrated and purified by column chromatography (dichloromethane:methanol=19:1) to give (R)-1-(3,4-(bis(benzyloxy) phenoxy)-3-((2-hydroxyethyl)amino)propan-2-ol (YOK-1106, 9.0 mg, yield: 85%). H NMR (CDCl$_3$, 300 MHz): δ 7.42-7.40 (m, 2H), 7.33-7.27 (m, 8H), 6.82 (d, 1H, J=9.0 Hz), 6.42 (d, 1H, J=3.0 Hz), 6.28 (dd, 1H, J=3.0 and 9.0 Hz), 5.09 (d, 1H, J=12.9 Hz), 5.06 (s, 2H), 4.93 (d, 1H, J=12.9 Hz), 4.35-4.25 (m, 1H), 3.94 (dd, 1H, J=3.6 and 9.9 Hz), 3.89-3.72 (m, 3H), 3.34 (t, 1H, J=11.4 Hz), 2.93 (brS, 2H), 2.80 (d, 1H, J=10.8 Hz); ESIMS m/z: 424.67[M+H]$^+$.

Example 2: Preparation of (R)-1-(3,4-(bis((4-chlorobenzyl)oxy)phenoxy)-3-((2-hydroxyethyl)amino) propan-2-ol (YT-6-1)

(R)-1-(3,4-(Bis((4-chlorobenzyl)oxy) phenoxy)-3-((2-hydroxyethyl)amino)propan-2-ol (YT-6-1) was synthesized in the same manner as in the preparation method of Example 19 by using 3,4-bis((4-chlorobenzyl)oxy)benzaldehyde (1101-1) instead of 3,4-bis(benzyloxy)benzaldehyde (1101) as a starting material. H NMR (400 MHz, DMSO-d$_6$) δ (ppm) 2.59 (m, 4H), 3.45 (s, 2H), 3.81 (m, 3H), 4.50 (b, 1H), 4.85 (b, 1H), 5.01 (s, 2H), 5.11 (s, 2H), 6.42 (dd, J=8 Hz and 2.8 Hz, 1H), 6.66 (d, J=2.8 Hz, 1H), 6.92 (d, J=8 Hz, 1H), 7.42 (s, 4H), 7.45 (s, 4H); ESI-MS Calcd m/z for C$_{25}$H$_{27}$Cl$_2$NO$_5$ [M+2]$^+$493.90 Found 492.39.

Example 3: Preparation of (R)-1-(3,4-(bis((4-fluorobenzyl)oxy)phenoxy)-3-((2-hydroxyethyl)amino) propan-2-ol (YT-6-2)

(R)-1-(3,4-(Bis((4-fluorobenzyl)oxy) phenoxy)-3-((2-hydroxyethyl)amino)propan-2-ol (YT-6-2) was synthesized in the same manner as in as the preparation method of Example 19 by using 3,4-bis((4-fluorobenzyl)oxy)benzaldehyde (1101-2) instead of 3,4-bis(benzyloxy)benzaldehyde (1101) as a staring material. $^1$H NMR (400 MHz, CDCl$_3$) δ (ppm) 2.82 (m, 4H), 3.69 (t, J=5.2 Hz, 2H), 3.91 (m, 2H), 4.05 (m, 1H), 5.00 (s, 2H), 5.06 (s, 2H), 6.41 (m, 1H), 6.58 (d, J=2.8 Hz, 1H), 6.84 (d, J=8 Hz, 1H), 7.03 (m, 4H), 7.37 (m, 4H); ESI-MS Calcd m/z for C$_{25}$H$_{27}$F$_2$NO$_5$ [M+2]$^+$461.0 Found 459.49.

Example 12: Preparation of (R)-1-(3,4-bis(benzyloxy)phenoxy)-3-(isopropylamino)propan-2-ol (YOK-1104)

(R)-1-(3,4-Bis(benzyloxy) phenoxy)-3-(isopropylamino) propan-2-ol (YOK-1104) was synthesized by using isopropyl amine instead of 2-aminoethan-1-ol in the preparation step 3 of Example 1. $^1$H NMR (300 MHz, CDCl$_3$) δ (ppm) 1.12 (d, J=6 Hz, 6H), 2.81 (m, 5H), 3.88 (d, J=3 Hz, 2H), 4.04 (m, 1H), 5.09 (d, J=15 Hz), 6.38 (dd, J=9 Hz and 3 Hz, 1H), 6.59 (s, 1H), 6.85 (d, J=9 Hz, 1H), 7.35 (m, 10H; ESI-MS Calcd m/z for C$_{26}$H$_{31}$NO$_4$ [M+H]$^+$ 422.42 Found 421.54.

Example 13: Preparation of (R)-1-(3,4-diphenethoxyphenoxy)-3-(isopropylamino)propan-2-ol (YOK-2204)

(R)-1-(3,4-diphenethoxyphenoxy)-3-(isopropylamino) propan-2-ol (YOK-2204) was synthesized in the same manner as in the preparation method of Example 1, except that in step 1 of the preparation method of Example 1, 3,4-diphenethoxybenzaldehyde (2201) was used as a starting material instead of 3,4-bis(benzyloxy)benzaldehyde (1101), and in step 3, isopropylamine was used instead of 2-aminoethan-1-ol. $^1$H NMR (300 MHz, CDCl$_3$) δ (ppm) 1.17 (d, J=6 Hz, 6H), 2.79 (dd, J=9 Hz and 3 Hz, 1H), 2.95 (m, 2H), 3.08 (m, 4H), 3.34 (b, 2H), 3.89 (m, 2H), 4.13 (m, 5H), 6.37 (dd, J=6 Hz and 3 Hz, 1H), 6.52 (d, J=3 Hz, 1H), 6.78 (d, J=9 Hz, 1H), 7.25 (m, 10H); ESI-MS Calcd m/z for C$_{28}$H$_{35}$NO$_4$ [M+H]$^+$ 451.00 Found 449.59.

Example 14: Preparation of (R)-1-(3,4-bis(3-phenylpropoxy)phenoxy)-3-(isopropylamino)propan-2-ol (YOK-3304)

(R)-1-(3,4-bis(3-phenylpropoxy)phenoxy)-3-(isopropylamino)propan-2-ol (YOK-3304) was synthesized in the same manner as in the preparation method of Example 1, except that in step 1 of the preparation method of Example 1, 3,4-bis(3-phenylpropoxy)benzaldehyde (3301) was used as a starting material instead of 3,4-bis(benzyloxy)benzaldehyde (1101), and step 3, isopropylamine was used instead of 2-aminoethan-1-ol. $^1$H NMR (300 MHz, CDCl$_3$) δ (ppm) 1.21 (d, J=6 Hz, 6H), 2.12 (m, 4H), 2.83 (t, J=9 Hz, 5H), 3.01 (m, 2H), 3.30 (b, 3H), 3.93 (m, 6H), 4.18 (m, 1H), 6.38 (dd, J=6 Hz and 3 Hz, 1H), 6.52 (d, J=3 Hz, 1H), 6.80 (d, J=9 Hz, 1H), 7.25 (m, 10H); ESI-MS Calcd m/z for C$_{30}$H$_{39}$NO$_4$ [M+H]$^+$ 479.09 Found 477.65.

Example 15: Preparation of (R)-1-(3,4-bis(4-phenylbutoxy)phenoxy)-3-(isopropylamino)propan-2-ol (YOK-4404)

(R)-1-(3,4-bis(4-phenylbutoxy) phenoxy)-3-(isopropylamino)propan-2-ol (YOK-4404) was synthesized in the same manner as in the preparation method of Example 1, except that in step 1 of the preparation method of Example 1, 3,4-bis(4-phenylbutoxy)benzaldehyde (4401) was used as a starting material instead of 3,4-bis(benzyloxy)benzaldehyde (1101), and in step 3, isopropylamine was used instead of 2-aminoethan-1-ol. $^1$H NMR (300 MHz, CDCl$_3$) δ (ppm) 1.26 (dd, J=6 Hz and 3 Hz, 8H), 1.81 (m, 7H), 2.66 (t, J=6 Hz, 4H), 2.85 (m, 1H), 3.06 (m, 2H), 3.46 (b, 2H), 3.93 (m, 6H), 4.24 (m, 1H), 6.36 (dd, J=6 Hz and 3 Hz, 1H), 6.52 (d, J=3 Hz, 1H), 6.78 (d, J=9 Hz, 1H), 7.23 (m, 10H), ESI-MS Calcd m/z for C$_{32}$H$_{43}$NO$_4$ [M+H]$^+$ 505.70 Found 503.45.

Example 18: Preparation of (R)-1-(3,4-bis((4-chlorobenzyl)oxy)phenoxy)-3-(isopropylamino)propan-2-ol (YT-4-1)

(R)-1-(3,4-bis((4-chlorobenzyl)oxy)phenoxy)-3-(isopropylamino)propan-2-ol (YT-4-1) was synthesized in the same manner as in the preparation method of Example 1, except that in step 1 of the preparation method of Example 1, 3,4-bis(4-chlorobenzyloxy)benzaldehyde (1101-1) was used as a starting material instead of 3,4-bis(benzyloxy)benzaldehyde (1101), and in step 3, isopropyl amine was used instead of 2-aminoethan-1-ol. $^1$H NMR (400 MHz, CDCl$_3$) δ (ppm) 1.08 (d, J=6.4 Hz, 6H), 2.68 (dd, J=12 Hz and 8 Hz, 1H), 2.83 (m, 2H), 3.88 (d, J=5.2 Hz, 2H), 3.95 (m, 1H), 5.01 (s, 2H), 5.06 (s, 2H), 6.40 (dd, J=8 Hz and 4 Hz, 1H), 6.56 (d, J=2.8 Hz, 1H), 6.82 (d, J=8 Hz, 1H), 7.31 (m, 8H); ESI-MS Calcd m/z for C$_{26}$H$_{29}$Cl$_2$NO$_4$ [M+H]$^+$ 491.40 Found 490.42.

Example 19: Preparation of (R)-1-(3,4-bis((4-fluorobenzyl)oxy)phenoxy)-3-(isopropylamino)propan-2-ol (YT-4-2)

(R)-1-(3,4-bis((4-fluorobenzyl)oxy)phenoxy)-3-(isopropylamino)propan-2-ol (YT-4-2) was synthesized in the same manner as in the preparation method of Example 1, except that in step 1 of the preparation method of Example 1, 3,4-bis(4-fluorobenzyloxy)benzaldehyde (1101-2) was used as a starting material instead of 3,4-bis(benzyloxy)benzaldehyde (1101), and in step 3, isopropyl amine was used instead of 2-aminoethan-1-ol. $^1$H NMR (400 MHz, CDCl$_3$) δ (ppm) 1.08 (d, J=6.4 Hz, 6H), 2.68 (dd, J=12 Hz and 8 Hz, 1H), 2.83 (m, 2H), 3.89 (d, J=4 Hz, 2H), 3.95 (m, 1H), 5.00 (s, 2H), 5.05 (s, 2H), 6.40 (dd, J=8 Hz and 2.8 Hz, 1H), 6.59 (d, J=2.8 Hz, 1H), 6.83 (d, J=9.6 Hz, 1H), 7.03 (m, 4H), 7.37 (m, 4H); ESI-MS Calcd m/z for C$_{26}$H$_{29}$F$_2$NO$_4$ [M+H]$^+$ 457.90 Found 457.52.

Preparation Example 2) The compounds of Examples 6 to 11 were synthesized according to the process shown in Reaction Scheme 2 below.

[Reaction Scheme 2]

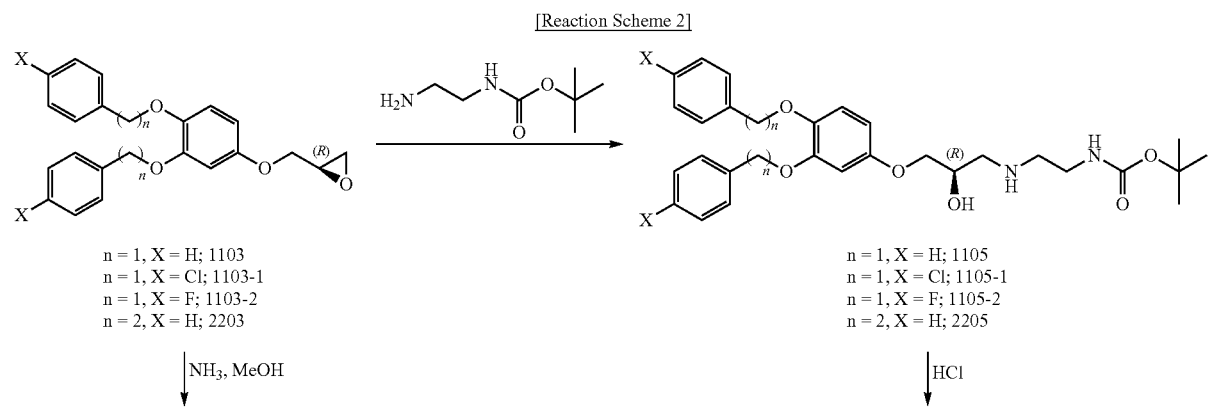

n = 1, X = H; 1103
n = 1, X = Cl; 1103-1
n = 1, X = F; 1103-2
n = 2, X = H; 2203 n = 1, X = H; 1105
n = 1, X = Cl; 1105-1
n = 1, X = F; 1105-2
n = 2, X = H; 2205

NH$_3$, MeOH

HCl

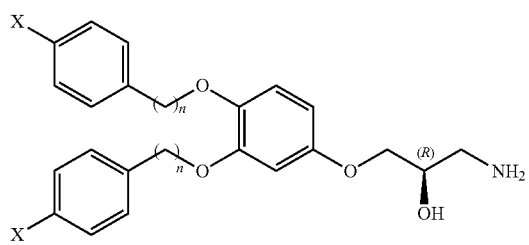

n = 1, X = H; 1107
n = 1, X = Cl; 1107-1
n = 1, X = F; 1107-2
n = 2, X = H; 2207

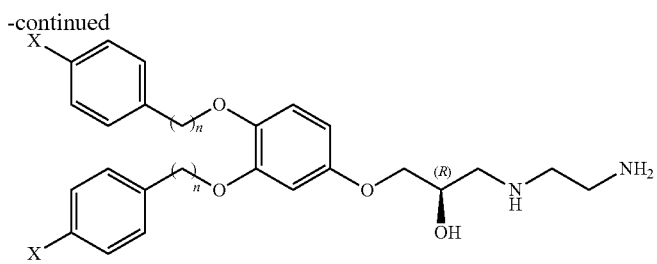

n = 1, X = H; 1106
n = 1, X = Cl; 1106-1
n = 1, X = F; 1106-2
n = 2, X = H; 2206

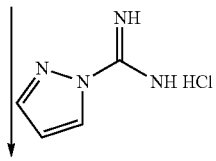

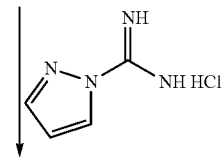

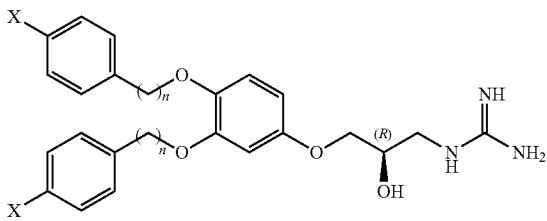

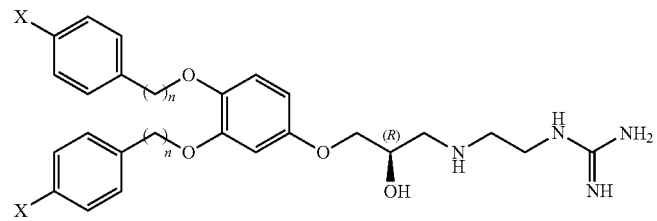

Example 6: Preparation of (R)-1-(2-((3-(3,4-bis(benzyloxy)phenoxy)-2-hydroxypropyl)amino)ethyl) guanidine (YOK-1109)

Step 1) After R-2-((3,4-bis(benzyloxy)phenoxy)methyl)oxirane (1103, 500 mg, 1.38 mmol) was dissolved in methanol (10 ml), tert-butyl 2-aminoethylcarbamate (442 mg, 2.76 mmol) was added thereto and stirred at 50° C. for 10 hours. When the reaction was completed, the reaction solvent is concentrated under reduced pressure.

Step 2) After tert-butyl (R)-(2-((3-(3,4-bis(benzyloxy)phenoxy)-2-hydroxypropyl)amino)ethyl)carbamate (1105, 600 mg, 1.15 mmol) was dissolved in methanol (3 ml), methanol/hydrochloric acid (3N, 2 ml) was added thereto, and then stirred at room temperature for 4 hours. When the reaction was completed, the reaction mixture was concentrated under reduced pressure (white solid, 1106) and used as a starting material in the next step without purification.

Step 3) (R)-1-((2-aminoethyl)amino)-3-(3,4-bis(benzyloxy)phenoxy)propan-2-ol (1106, 400 g, 0.95 mmol) was dissolved in DMF (3 ml), and then 1H-pyrazole-1-carboxamidine hydrochloride (553 mg, 3.8 mmol) and diisopropylethylamine (0.3 g, 2.4 mmol) were further added thereto. The reaction mixture was stirred at 30° C. for 12 hours, concentrated under reduced pressure and purified by high resolution liquid chromatography to synthesize (R)-1-(2-((3-(3,4-bis(benzyloxy)phenoxy)-2-hydroxypropyl)amino)ethyl)guanidine (YOK-1109, 22 mg) as a white solid. $^1$H NMR (400 MHz, DMSO+D$_2$O) δ (ppm) 3.13 (m, 4H), 3.47 (s, 2H), 3.89 (s, 2H), 5.04 (s, 2H), 5.12 (s, 2H), 6.46 (d, J=8 Hz, 1H), 6.67 (s, 1H), 6.97 (d, J=8 Hz, 1H), 7.39 (m, 10H); ESI-MS Calcd m/z for C$_{26}$H$_{32}$N$_4$O$_4$ [M+H]$^+$ 465.00 Found 464.57.

Example 7: Preparation of (R)-1-(2-((3-(3,4-diphenethoxyphenoxy)-2-hydroxypropyl)amino)ethyl)guanidine (YOK-2209)

(R)-1-(2-((3-(3,4-diphenethoxyphenoxy)-2-hydroxypropyl)amino)ethyl)guanidine (YOK-2209) was synthesized in the same manner as in the preparation method of Example 6, except that R-2-((3,4-diphenethoxyphenoxy)methyl)oxirane (2203) was used instead of R-2-((3,4-bis(benzyloxy)phenoxy)methyl)oxirane (1103) in step 1 of the preparation method of Example 6. $^1$H NMR (400 MHz, CD$_3$OD) δ (ppm) 3.00 (t, J=6.8 Hz, 2H), 3.06 (t, J=6.8 Hz, 2H), 3.23 (m, 1H), 3.28 (m, 3H), 3.62 (t, J=6.4 Hz, 2H), 6.46 (dd, J=8 Hz and 2.8 Hz, 1H), 6.60 (d, J=2.8 Hz, 1H), 6.85 (d, J=8 Hz, 1H), 7.25 (m, 10H); ESI-MS Calcd m/z for C$_{28}$H$_{36}$N$_4$O$_4$ [M+H]$^+$ 493.00 Found 492.62.

Example 8: Preparation of (R)-1-(2-((3-(3,4-bis(4-chlorobenzyl)oxy)phenoxy)-2-hydroxypropyl)amino)ethyl)guanidine (YT-9-1)

(R)-1-(2-((3-(3,4-bis(4-chlorobenzyl)oxy)phenoxy)-2-hydroxypropyl)amino)ethyl)guanidine (YT-9-1) was synthesized in the same manner as in the preparation method of Example 6, except that R-2-((3,4-bis(4-chlorobenzyl)oxy)phenoxy)methyl)oxirane (1103-1) was used instead of 1103 in step 1 of the preparation method of Example 6. $^1$H NMR (400 MHz, DMSO+D$_2$O) δ (ppm) 3.13 (m, 4H), 3.47 (t, J=6 Hz, 2H), 3.90 (m, 2H), 4.13 (m, 1H), 5.03 (s, 2H), 5.10 (s, 2H), 6.47 (dd, J=8 Hz and 2 Hz, 1H), 6.66 (d, J=2.4 Hz, 1H), 6.97 (d, J=8.8 Hz, 1H), 7.42 (s, 4H), 7.45 (s, 4H); ESI-MS Calcd m/z for C$_{26}$H$_{30}$Cl$_2$N$_4$O$_4$ [M+H]$^+$ 532.90 Found 533.45.

Example 9: Preparation of (R)-1-(2-((3-(3,4-bis(4-fluorobenzyl)oxy)phenoxy)-2-hydroxypropyl)amino)ethyl)guanidine (YT-9-2)

(R)-1-(2-((3-(3,4-bis(4-fluorobenzyl)oxy)phenoxy)-2-hydroxypropyl)amino)ethyl)guanidine (YT-9-2) was synthesized in the same manner as in the preparation method of Example 6, except that R-2-((3,4-bis(4-fluorobenzyl)oxy)phenoxy)methyl)oxirane (1103-2) was used instead of 1103 in step 1 of the preparation method of Example 6. $^1$H NMR (400 MHz, DMSO-$d_6$) δ (ppm) 3.13 (m, 4H), 3.45 (t, J=6 Hz, 2H), 3.89 (m, 2H), 4.15 (m, 1H), 5.01 (s, 2H), 5.09 (s, 2H), 6.46 (dd, J=8 Hz and 2.8 Hz, 1H), 6.68 (d, J=2.8 Hz, 1H), 6.96 (d, J=9.2 Hz, 1H), 7.20 (m, 4H), 7.46 (m, 4H); ESI-MS Calcd m/z for $C_{26}H_{30}Cl_2N_4O_4$ [M+H]$^+$ 501.00 Found 500.55.

Example 10: Preparation of (R)-1-(3-(3,4-bis(benzyloxy)phenoxy)-2-hydroxypropyl)guanidine (YOK-1107)

Step 1) After R-2-((3,4-bis(benzyloxy)phenoxy)methyl)oxirane (1103, 500 mg, 1.38 mmol) was dissolved in methanol (10 ml), ammonia/methanol (2N, 3 ml) was added thereto and stirred at 50° C. for 10 hours. When the reaction was completed, the reaction solvent was concentrated under reduced pressure.

Step 2) (R)-1-amino-3-(3,4-bis(benzyloxy)phenoxy)propan-2-ol (1107, 300 mg, 0.8 mmol) was dissolved in DMF (3 ml), and then 1H-pyrazole-1-carboxamidine hydrochloride (570 mg, 3.9 mmol) and diisopropylethylamine (0.3 g, 2.4 mmol) were added sequentially. The reaction mixture was stirred at 30° C. for 12 hours, concentrated under reduced pressure and purified by high resolution liquid chromatography to synthesize (R)-1-(3-(3,4-bis(benzyloxy)phenoxy)-2-hydroxypropyl)guanidine (YOK-1107, 23 mg). $^1$H NMR (400 MHz, DMSO-$d_6$) δ (ppm) 3.20 (m, 1H), 3.31 (m, 1H), 5.03 (s, 2H), 5.12 (s, 2H), 6.44 (dd, J=8.8 Hz and 2.8 Hz, 1H), 6.68 (d, J=2.8 Hz, 1H), 6.95 (d, J=8 Hz, 1H), 7.38 (m, 10H); ESI-MS Calcd m/z for $C_{24}H_{27}N_3O_4$ [M+H]$^+$ 422.00 Found 421.50.

Example 11: Preparation of (R)-1-(3-(3,4-diphenethoxyphenoxy)-2-hydroxypropyl)guanidine (YOK-2207)

(R)-1-(3-(3,4-diphenoxyphenoxy)-2-hydroxypropyl)guanidine (YOK-2207, 25 mg) was synthesized in the same manner as in the preparation method of Example 10, except that R-2-((3,4-diphenoxyphenoxy)methyl)oxirane (2203) was used instead of 1103 in step 1 of the preparation method of Example 10. $^1$H NMR (400 MHz, CD$_3$OD) δ (ppm) 3.00 (t, J=8 Hz, 2H), 3.06 (t, J=8 Hz, 2H), 3.33 (m, 1H), 3.42 (dd, J=24 Hz and 4 Hz, 1H), 3.91 (m, 2H), 4.08 (m, 3H), 4.16 (t, J=6.4 Hz, 2H), 6.46 (dd, J=8 Hz and 2 Hz, 1H), 6.60 (d, J=2.8 Hz, 1H), 6.84 (d, J=8 Hz, 1H), 7.25 (m, 10H); ESI-MS Calcd m/z for $C_{26}H_{31}N_3O_4$ [M+H]$^+$ 450.00 Found 449.55.

Preparation Example 3) Compounds of Examples 4 and 5 were synthesized by the method shown in Reaction Scheme 3 below.

[Reaction Scheme 3]

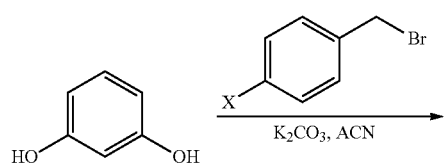

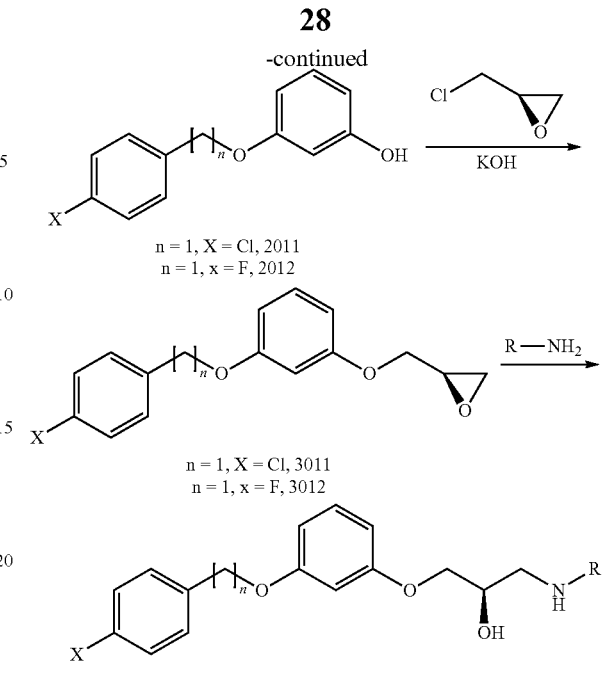

Example 4: Preparation of (R)-1-(3-((4-chlorobenzyl)oxy)phenoxy)-3-((2-hydroxyethyl)amino)propan-2-ol (YT-6-7)

Step 1) 1,3-Dihydroxybenzene (5.0 g, 45.4 mmol) was dissolved in acetonitrile (100 ml) and then K$_2$CO$_3$ was added thereto. Then, 1-(bromomethyl)-4-chlorobenzene (9.3 g, 45.4 mmol) was added to the reaction and then stirred at 80° C. for 16 hours. After cooling to room temperature, the reaction solvent was concentrated under reduced pressure. Water was added to the concentrated residue, followed by extraction with ethyl acetate. The organic layer was dehydrated with anhydrous sodium sulfate and filtered under reduced pressure. The filtrate was taken, concentrated under reduced pressure, and then purified by column chromatography (ethyl acetate/petroleum ether 1:15 to 1:8) to synthesize 3-((4-chlorobenzyl)oxy)phenol (2011, 2.3 g) as a light yellow oil. 1H NMR (400 MHz, CD$_3$OD) δ (ppm) 5.03 (s, 2H), 6.35-6.43 (m, 3H), 7.04 (t, 1H), 7.45 (s, 4H), 9.41 (s, 1H).

Step 2) After 3-((4-chlorobenzyl)oxy)phenol (2011, 1.0 g, 4.2 mmol) was dissolved in ethanol (10 ml), (R)-2-(chloromethyl)oxirane (1.17 g, 12.7 mmol), purified water (1 ml), and KOH (0.24 g, 4.2 mmol) were added, and then stirred at room temperature for hours. Water (30 ml) was added to the reaction and extracted with ethyl acetate (30 ml). The aqueous layer was extracted twice more with ethyl acetate, and then the organic layer was dehydrated with anhydrous sodium sulfate and filtered under reduced pressure. The filtered solution was concentrated under reduced pressure and purified by column chromatography (ethyl acetate/petroleum ether 1:15 to 1:8) to synthesize (R)-2-((3-((4-chlorobenzyl)oxy)phenoxy)methyl)oxirane (3011, 0.85 g) as a colorless oil. $^1$H NMR (400 MHz, CD$_3$OD) δ (ppm) 2.74 (m, 1H), 2.90 (m, 1H), 3.34 (m, 1H), 3.91-3.95 (m, 1H), 4.18-4.22 (m, 1H), 5.01 (s, 2H), 6.52-6.59 (m, 3H), 7.16-7.26 (m, 1H), 7.35 (s, 4H).

Step 3) (R)-2-((3-((4-chlorobenzyl)oxy)phenoxy)methyl)oxirane (3011, 300 mg, 1.03 mmol) was dissolved in methanol (5 ml), and then 2-aminoethanol (189 mg, 3.09 mmol) was added thereto. The reaction mixture was stirred at 65°

C. for 5 hours. After cooling to room temperature, the reaction solvent was concentrated under reduced pressure and purified by high resolution liquid chromatography to synthesize (R)-1-(3-((4-chlorobenzyl)oxy)phenoxy)-3-((2-hydroxyethyl)amino)propan-2-ol (YT-6-7, 15 mg) as a white solid. $^1$H NMR (400 MHz, CDCl$_3$) δ (ppm) 2.83 (m, 4H), 3.69 (m, 2H), 2.96 (m, 2H), 4.08 (m, 1H), 5.00 (s, 2H), 6.55 (m, 3H), 7.18 (t, J=8 Hz, 1H), 7.35 (s, 4H); ESI-MS Calcd m/z for C$_{18}$H$_{22}$ClNO$_4$ [M]$^+$352.00 Found 351.83.

Example 5: Preparation of (R)-1-(3-((4-fluorobenzyl)oxy)-3-((2-hydroxyethyl)amino)propan-2-ol (YT-6-8)

(R)-1-(3-((4-fluorobenzyl)oxy) phenoxy)-3-((2-hydroxyethyl)amino)propan-2-ol (YT-6-8, 20 mg) was synthesized in the same manner as in the preparation method of Example 4, except that 1-(bromomethyl)-4-fluorobenzene was used instead of 1-(bromomethyl)-4-chlorobenzene in step 1 of the preparation method of Example 4. $^1$H NMR (400 MHz, CDCl$_3$) δ (ppm) 2.03 (b, 3H), 2.83 (m, 4H), 3.69 (t, J=4.8 Hz, 2H), 3.96 (m, 2H), 4.08 (m, 1H), 4.99 (s, 2H), 6.56 (m, 3H), 7.07 (m, 2H), 7.18 (t, J=8 Hz, 1H), 7.40 (m, 2H); ESI-MS Calcd m/z for C$_{18}$H$_{22}$FNO$_4$ [M+H]$^+$ 336.00 Found 335.38.

Preparation Example 4) The compounds of Examples and 17 were synthesized by the method shown Reaction Scheme 4 below.

[Reaction Scheme 4]

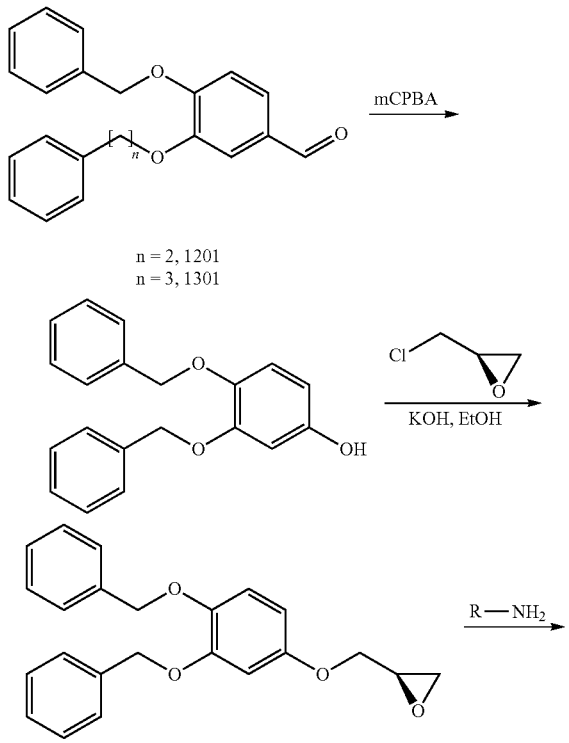

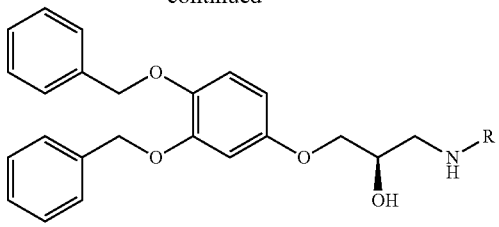

Example 16: Preparation of (R)-1-(4-(benzyloxy)-3-phenethoxyphenoxy)-3-(isopropylamino)propan-2-ol (YOK-1204)

Step 1) After 4-(benzyloxy)-3-phenethoxybenzaldehyde (1201, 332 mg, 1.0 mmol) was dissolved in dichloromethane, m-chloroperbenzoic acid (mCPBA, 260 mg, 1.5 mmol) is added thereto and then stirred at room temperature for 4 hours. An excess of ethyl acetate was added to the reaction, and then washed with saturated aqueous sodium carbonate solution, and the organic layer was separated. The organic layer was washed with an aqueous sodium chloride solution, then dehydrated with anhydrous sodium sulfate and filtered under reduced pressure.

The filtered solution was concentrated and dissolved again in methanol (10 ml), then 6N NaOH was added and stirred at room temperature for 30 minutes. 4N HCl solution was added to the reaction and then further stirred for 30 minutes. The reaction mixture was diluted with ethyl acetate (50 ml), then washed with brine, dehydrated with anhydrous sodium sulfate, and filtrated under reduced pressure. The filtered solution was concentrated and then purified by column chromatography (hexane/ethyl acetate ratio=7/3) to give 4-(benzyloxy)-3-phenoxyphenol (1202, 310 mg, yield: 90%). 1H NMR (CDCl3, 300 MHz) δ (ppm): 7.23-7.42 (m, 10H), 6.77 (d, 1H, J=9.0 Hz), 6.46 (d, 1H), 6.28 (dd, 1H, J=3.0 and 9.0 Hz), 4.98 (s, 2H), 4.58 (s, 1H), 4.20 (t, 2H, J=6 Hz), 3.14 (t, 2H, J=6 Hz).

Step 2) 4-(Benzyloxy)-3-phenethoxyphenol (1202, 320 mg, 1.0 mmol) was diluted with ethanol (5 ml), and then KOH aqueous solution (KOH 66 mg, 1.2 mmol, 1 ml) and (R)-2-(chloromethyl)oxirane (410 ul, 5.0 mmol) were added sequentially. The reaction mixture was stirred at room temperature for 5 hours, and then the organic solvent was removed under reduced pressure. The concentrated reaction mixture was diluted again with ethyl acetate, washed with water and then with brine. The extracted organic layer was dehydrated with anhydrous sodium sulfate and then filtered under reduced pressure. The filtered organic layer was concentrated and purified by column chromatography to give pure R-2-((4-(benzyloxy)-3-phenethoxyphenoxy)methyl)oxirane (1203, 308 mg, yield: 82%). $^1$H NMR (300 MHz, CDCl$_3$) δ (ppm) 7.44-7.47 (m, 2H), 7.26-7.39 (m, 5H), 7.19-7.22 (m, 3H), 6.84 (d, 1H, J=6.0 Hz), 6.54 (d, 1H, J=3.0 Hz), 6.36 (dd, 1H), 5.07 (s, 2H), 4.15 (dd, 1H), 4.00 (t, 2H, J=6.0 Hz), 2.84 (t, 2H, J=9.0 Hz), 2.73 (dd, 1H), 2.10-2.19 (m, 2H); ESIMS m/z: 363.5 [M+H]$^+$.

Step 3) After R-2-((4-(benzyloxy)-3-phenethoxyphenoxy)methyl)oxirane (1203, 9.4 mg, 25 nmol) was diluted with anhydrous ethanol (1 ml), isopropylamine (10 μL, 125 nmol) was added thereto and stirred at room temperature for 4 hours. After confirming the reaction by TLC, the reaction solvent was concentrated under reduced pressure, and water was added to the concentrated reaction product and extracted with dichloromethane (3×5 mL). The extracted organic layer was dehydrated with anhydrous sodium sulfate and then filtered under reduced pressure. The filtered organic layer was concentrated and purified by column chromatography (dichloromethane:methanol=19:1) to give (R)-1-(4-(benzyloxy)-3-phenethoxyphenoxy)-3-(isopropylamino)propan-2-ol (YOK-1204, 9.3 mg, yield: 86%). $^1$H NMR (300 MHz, CDCl$_3$) δ (ppm) 1.15 (d, J=6 Hz, 6H), 2.71 (m, 4H), 2.80 (m, 2H), 3.14 (t, J=6 Hz, 2H), 3.91 (d, J=3 Hz, 2H), 4.09 (m, 1H), 4.21 (t, J=6 Hz, 2H), 4.99 (s, 2H), 6.35 (dd, J=6 Hz and 3 Hz, 1H), 6.54 (d, J=3 Hz, 1H), 6.82 (d, J=9 Hz, 1H), 7.26 (m, 10H); ESI-MS Calcd m/z for C$_{27}$H$_{33}$NO$_4$ [M+H]$^+$ 437.00 Found 435.56.

Example 17: Preparation of (R)-1-(4-(benzyloxy)-3-(3-phenylpropoxy)phenoxy)-3-(isopropylamino)propan-2-ol (YOK-1304)

(R)-1-(4-(benzyloxy)-3-(3-phenylpropoxy)phenoxy)-3-(isopropylamino)propan-2-ol (YOK-1304, 9.5 mg, yield: 85%) as a while solid was synthesized in the same manner as in the preparation method of Example 16, by using 4-(benzyloxy)-3-(3-phenylpropoxy)benzaldehyde (1301, 346 mg, 1.0 mmol) instead of 4-(benzyloxy)-3-phenethoxybenzaldehyde (1201) as a starting material in step 1 of the preparation method of Example 16. 1H NMR (300 MHz, CDCl$_3$) δ (ppm) 1.13 (d, J=6 Hz, 6H), 2.15 (m, 2H), 2.33 (b, 3H), 2.80 (m, 5H), 3.91 (d, J=6 Hz, 2H), 4.01 (m, 3H), 5.07 (s, 2H), 6.36 (dd, J=6 Hz and 3 Hz, 1H), 6.53 (d, J=3 Hz, 1H), 6.84 (d, J=9 Hz, 1H), 7.33 (m, 10H); ESI-MS Calcd m/z for C$_{28}$H$_{35}$NO$_4$ [M+H]$^+$ 451.00 Found 449.59.

Preparation Example 5) The compounds of Comparative Examples 1 and 2 were synthesized by the method shown in Reaction Scheme 5 below.

[Reaction Scheme 5]

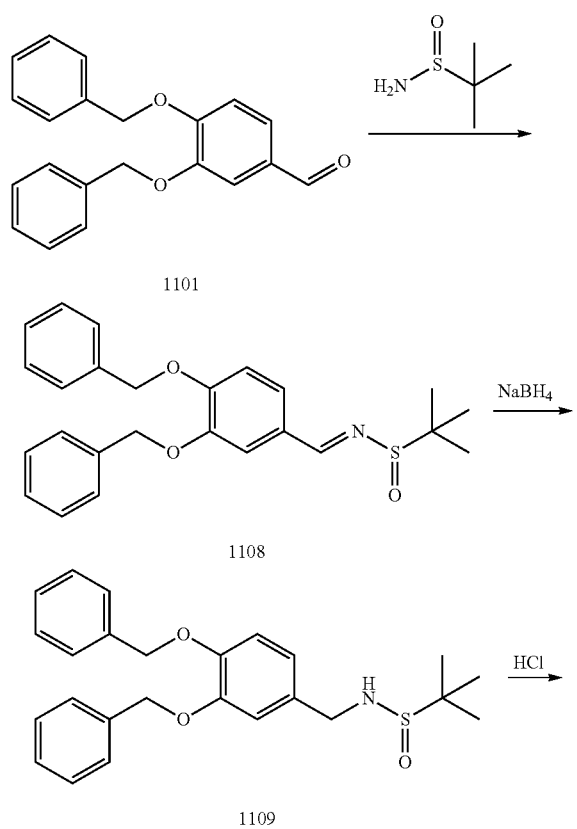

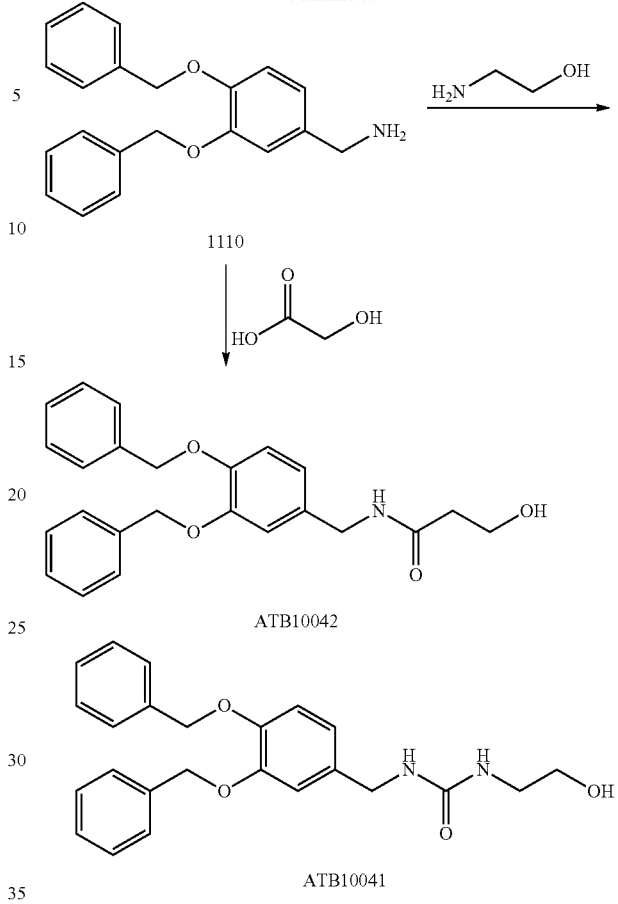

Comparative Example 1: Preparation of methyl (R)-(3-(3,4-bis(benzyloxy)phenoxy)-2-hydroxypropyl)glycineate (YOK-G-1104)

Methyl (R)-(3-(3,4-bis(benzyloxy)phenoxy)-2-hydroxypropyl)glycineate (YOK-G-1104) was synthesized in the same manner as in the preparation method of Example 19, except that glycine methyl ester was used instead of 2-aminoethan-1-ol in step 3 of the preparation method of Example 19. $^1$H NMR (300 MHz, DMSO-d$_6$) δ (ppm) 2.55 (m, 1H), 2.81 (m, 1H), 3.51 (s, 2H), 3.66 (s, 3H), 4.05 (m, 1H), 4.20 (m, 2H), 5.16 (s, 2H), 5.18 (s, 2H), 5.37 (br s, 1H), 5.52 (br s, 1H), 6.57 (s, 1H), 6.67 (d, 1H), 6.96 (d, 1H), 7.32-7.48 (m, 10H).

Comparative Example 2: Preparation of ethyl (R)-(3-(3,4-bis(benzyloxy)phenoxy)-2-hydroxypropyl)alanineate (YOK-A-1104)

Ethyl (R)-(3-(3,4-bis(benzyloxy)phenoxy)-2-hydroxypropyl)alanineate (YOK-A-1104) was synthesized in the same manner as in the preparation method of Example 19, except that alanine ethyl ester was used instead of 2-aminoethan-1-ol in step 3 of the preparation method of Example 19. $^1$H NMR (300 MHz, DMSO-d$_6$) δ (ppm) 1.21 (t, 3H), 1.27 (m, 3H), 2.56-2.81 (m, 2H), 3.56 (m, 1H), 4.05 (m, 1H), 3.95-4.20 (m, 4H), 5.16 (s, 2H), 5.18 (s, 2H), 5.37 (br s, 1H), 6.57 (s, 1H), 6.67 (d, 1H), 6.96 (d, 1H), 7.32-7.48 (m, 10H).

Experimental Example 1. Evaluation of
Oligomerization Activity of p62 Protein in Cultured
Cells by Immunoblotting In order to evaluate the p62 protein oligomerization activity efficacy by the compounds (Examples 1-19), HEK293 cell line, which is human embryonic kidney-derived cell, was collected. As representative compounds among the present compounds, YOK-1104, YOK-2204, YOK-3304, YOK-1204, YOK-4404, YOK-1107, YOK-1109, YOK-2207, YOK-2209, YT-4-1, YT-4-2, YT-6-1, YT-6-2, YT-6-7, YT-6-8, YT-9-1, YT-9-2 were selected. In order to measure intracellular p62 protein activation and oligomerization according to the treatment with these selected representative compounds, the respective cells were dispensed into a pi dish. The cells were collected after further culturing for 24 hours so that the cells were completely attached to the surface of the plate. 100 ul of lysis buffer (20 mM Tris, pH 7.4), 150 mM NaCl, 1% Triton X-100, 2 mM NaF, 2 mM EDTA, 2 mM beta-glycerophosphate, 5 mM sodium orthovanadate, 1 mM PMSF, leupeptin, aprotinin) were injected into each sample and the cells were lysed. Based on the measured total protein concentration, each sample was treated with test compounds at room temperature for 2 hours, and then a sample buffer was added and allowed to react at 95° C. for 10 minutes. 25 ul was taken from the samples after the reaction, and dispensed into each well of acrylamide gel, and then immunoblotting was performed. Immunoblotting showed representative results from three or more independent experiments. The results are shown in FIG. 2.

As seen in FIG. 2, when treated with the p62 ligand compounds according to the present invention, it was confirmed that the treatment with the compounds resulted in a decrease of the monomer of p62 protein and simultaneously an increase in oligomers and high-molecular aggregates.

Experimental Example 2. Evaluation of Autophagy
Activity in Cultured Cells by Immunoblotting In order to evaluate the autophagy activity efficacy by the compounds (Examples 1-19), HeLa cell line, which is a cell line derived from a cervical cancer patient, was cultured using a DMEM medium containing 10% FBS and 1% streptomycin/penicillin in an incubator with 5% carbon dioxide. As representative compounds among the present compounds, YOK-1107, YOK-4404 and YOK-1104 were selected. In order to measure autophagy activity according to the treatment with these selected representative compounds, the respective cells were dispensed into 6 well plates. Additional cultures were performed for hours so that the cells were completely attached to the surface of the plate. To find the concentration at which the respective compounds could increase the phenomenon of autophagy, the test compounds were diluted at 1, 2, 5, 10 and 20 μM and treated. After treatment with the respective compounds, the cells were cultured again in a cell incubator for 24 hours, and then the cells were collected. To extract proteins from the collected cells, 100 ul of lysis buffer (20 mM Tris (pH 7.4), 150 mM NaCl, 1% Triton X-100, 2 mM NaF, 2 mM EDTA, 2 mM beta-glycerophosphate, 5 mM sodium orthovanadate, 1 mM PMSF, leupeptin, aprotinin) was injected into each sample, and cells were lysed. Based on the measured total protein concentration, a sample buffer was added to each sample and allowed to react at 100° C. for 5 minutes. 5 ul was taken from the samples after the reaction, and dispensed into each well of acrylamide gel, and then immunoblotting was performed. Immunoblotting showed representative results from three or more independent experiments. The results are shown in FIG. 3.

As seen in FIG. 3, when treated with the p62 ligand compounds according to the present invention, it was confirmed that the level of LC3, a marker of macroautophagy activity, gradually increased according to the concentration of the compounds.

Experimental Example 3. Evaluation of Autophagy
Activity in Cultured Cells by Immunoblotting In order to investigate the autophagy activity efficacy by the compounds (Examples 1-19), immunoblotting was performed in the same manner as in Experimental Example 2 using LC3 as a marker. As for the difference, in order to evaluate the treatment time required for activation and the activity retention time, as the representative compounds selected among the present compounds, 5 μM of YOK-1107, YOK-1204, YOK-1304, YOK-2204, YOK-3304, YOK- were treated for 1, 3, 6, 12, 24, 48 hours. On the other hand, as the representative compounds selected among the compounds of the present invention, μM of YOK-1107, YOK-1109, YOK-2207, YOK-2209, YT-4-1, YT-4-2, YT-6-1, YT-6-2, YT-6-8, YT-6-7, YT-9-1, YT-9-2 were treated for 24 hours. Immunoblotting showed representative results from three or more independent experiments. The results are shown in FIG. 4. As seen in FIG. 4, when treated with the p62 ligand compounds according to the present invention, it was confirmed that the level of LC3, a marker of macroautophagy activity, gradually increased according to the treatment with the compounds.

Experimental Example 4. Evaluation of Autophagy
Activity in Cultured Cells by Immunoblotting In order to investigate the autophagy activity efficacy of control compounds, immunoblotting was performed in the same manner as in Experimental Example 2 by using LC3 as a marker. As the control compounds, compounds having the following structure were used.

TABLE 2

| No. | Structure | Name of Compound |
|---|---|---|
| 1101 | 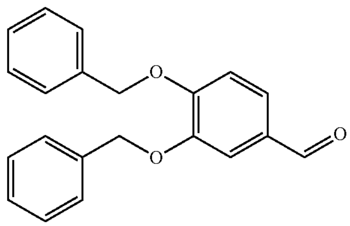 [SMILES: O=Cc1ccc(OCc2ccccc2)c(OCc2ccccc2)c1] | 3,4-bis(benzyloxy)benzaldehyde |
| 1102 | 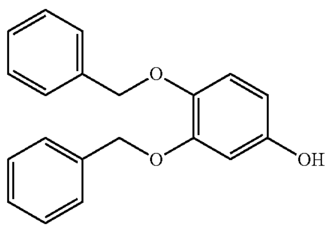 [SMILES: Oc1ccc(OCc2ccccc2)c(OCc2ccccc2)c1] | 3,4-bis(benzyloxy)phenol |
| 1103 | 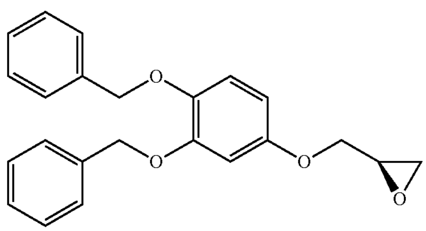 [SMILES: c1ccc(COc2ccc(OC[C@H]3CO3)cc2OCc2ccccc2)cc1] | (R)-2-((3,4-bis(benzyloxy)phenoxy)methyl)oxirane |
| 1201 | 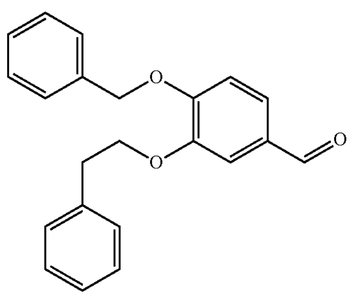 [SMILES: O=Cc1ccc(OCc2ccccc2)c(OCCc2ccccc2)c1] | 4-(benzyloxy)-3-phenethoxybenzaldehyde |
| 1202 | 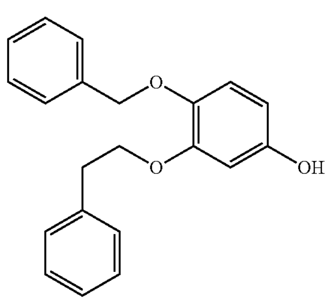 [SMILES: Oc1ccc(OCc2ccccc2)c(OCCc2ccccc2)c1] | 4-(benzyloxy)-3-phenethoxyphenol |
| 1203 | 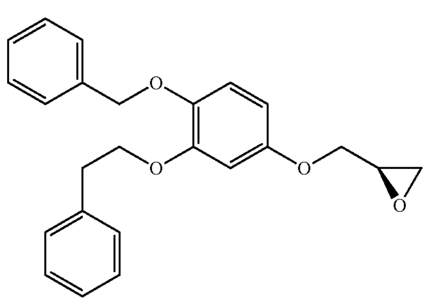 [SMILES: c1ccc(CCOc2cc(OC[C@H]3CO3)ccc2OCc2ccccc2)cc1] | (R)-2-((4-(benzyloxy)-3-phenethoxyphenoxy)methyl)oxirane |

TABLE 2-continued

| No. | Structure | Name of Compound |
|---|---|---|
| 1301 | 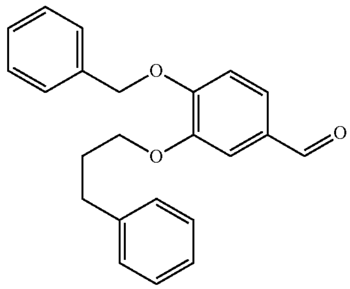 [SMILES: O=Cc1ccc(OCc2ccccc2)c(OCCCc2ccccc2)c1] | 4-(benzyloxy)-3-(3-phenylpropoxy)benzaldehyde |
| 1302 | 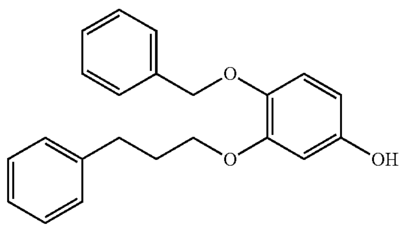 [SMILES: Oc1ccc(OCc2ccccc2)c(OCCCc2ccccc2)c1] | 4-(benzyloxy)-3-(3-phenylpropoxy)phenol |
| YTK-1105-1 | 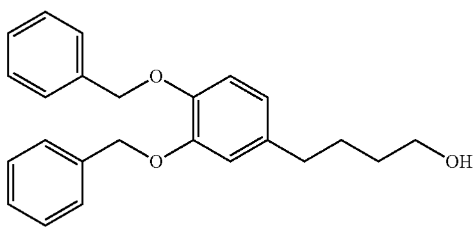 [SMILES: OCCCCc1ccc(OCc2ccccc2)c(OCc2ccccc2)c1] | 4-(3,4-bis(benzyloxy)phenyl)butan-1-ol |
| 4402 | 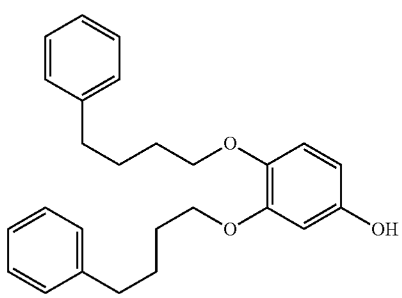 [SMILES: Oc1ccc(OCCCCc2ccccc2)c(OCCCCc2ccccc2)c1] | 3,4-bis(4-phenylbutoxy)phenol |
| 1401 | 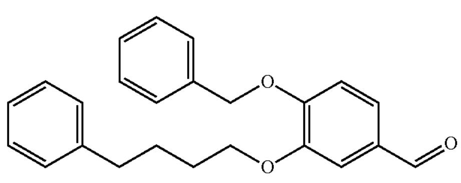 [SMILES: O=Cc1ccc(OCc2ccccc2)c(OCCCCc2ccccc2)c1] | 4-(benzyloxy)-3-(4-phenylbutoxy)benzaldehyde |
| 1402 | 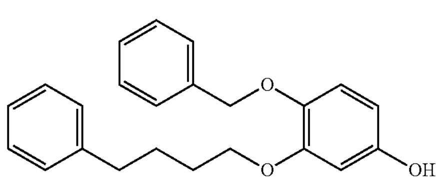 [SMILES: Oc1ccc(OCc2ccccc2)c(OCCCCc2ccccc2)c1] | 4-(benzyloxy)-3-(4-phenylbutoxy)phenol |

TABLE 2-continued

| No. | Structure | Name of Compound |
|---|---|---|
| 2201 | 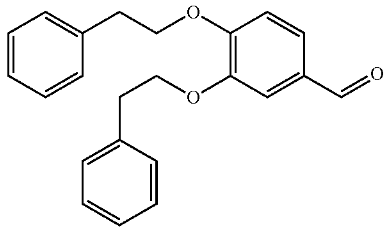 [SMILES: O=Cc1ccc(OCCc2ccccc2)c(OCCc2ccccc2)c1] | 3,4-diphenethoxybenzaldehyde |
| 2202 | 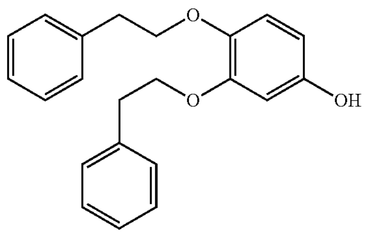 [SMILES: Oc1ccc(OCCc2ccccc2)c(OCCc2ccccc2)c1] | 3,4-diphenethoxyphenol |

The aforementioned compounds were confirmed by treatment at different concentrations and for different times, and immunoblotting showed representative results from three or more independent experiments. The results are shown in FIG. 5. As shown in FIG. 5, it was confirmed that the control compounds did not increase the level of LC3, a marker of macroautophagy activity, regardless of the treatment time or concentration.

Experimental Example 5. Evaluation of Autophagy Activity in Cultured Cells by Immunofluorescence Staining and Confocal Microscopy In order to confirm the p62 protein activity and the activity level of autophagy phenomenon by the compounds (Examples 1-19), immunofluorescence staining was performed using p62 and LC3 as markers. In order to confirm the p62 activity and the activity level of autophagy phenomenon by new p62 ligands and isomers thereof in cultured cells, HeLa cell line, which is a cell line derived from cervical cancer patient, was treated with the novel p62 ligand compounds (YOK-1106, YOK-1204, YOK-1504, YOK-2204, YOK-3304, YOK-4404, YOK-1107, YOK-1109, YOK-2207, YOK-2209, YT-4-1, YT-4-2, YT-6-1, YT-9-1 and YT-9-2) and cultured. Thereafter, as markers of the autophagy phenomenon, the expression level and location of LC3 puncta and the local co-existence with p62 puncta were observed.

For immunofluorescence staining, a cover glass was placed on a 24-well plate, cells were dispensed, cultured for 24 hours, and then treated with 5 uM of the novel p62 ligands according to the present invention. For the action of the compounds, additional cultures were performed for 24 hours, and then the medium was removed. Cells were fixed using formaldehyde at room temperature. In order to prevent non-specific staining, the cells were allowed to react with a blocking solution at room temperature for 1 hour, and then treated with LC3 antibody diluted at a certain ratio using the blocking solution, and allowed to reacted at room temperature for 1 hour. The antibody-treated cells were washed three times with PBS, and goat-derived secondary antibody was diluted at a certain ratio using the blocking solution, and then allowed to react at room temperature for 30 minutes. The cells were washed again with PBS three times, and for intracellular nuclear staining, the expression level, intracellular puncta formation and intracellular coexistence level of p62 and LC3 were observed through a confocal microscopy after DAPI staining. The results are shown in FIG. 5. Immunofluorescence staining showed representative results from three or more independent experiments.

As seen in FIG. 6, it was confirmed that after treatment with p62 ligand compounds according to the present invention, the intracellular puncta of p62 protein was formed, the intracellular puncta and local coexistence of LC3 as an autophagosome marker were increased, and the intracellular puncta formation of LC3 was increased.

Experimental Example 6. Evaluation of Autophagy Activity in Cultured Cells by Immunofluorescence Staining and Confocal Microscopy In order to confirm p62 protein activity and the activity level of autophagy phenomenon of control compounds (YOK-A-1104, YOK-G-1104, YTK-1005, YTK-1105-1), immunofluorescence staining was performed in the same manner as in Experimental Example 4 by using p62 and LC3 as markers. YOK-A-1104 and YOK-G-1104 are compounds having the following structures.

TABLE 3

| No. | Structure | Name of Compound |
| --- | --- | --- |
| YOK-A-1104 | 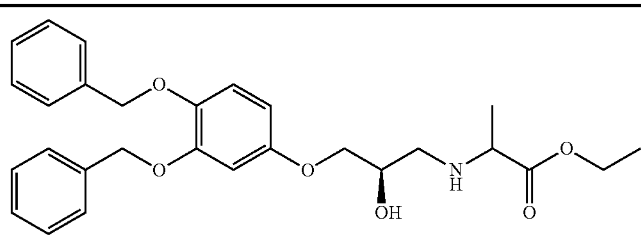 | Ethyl (R)-(3-(3,4-bis(benzyloxy)phenoxy)-2-hydroxypropyl)alanineate |
| YOK-G-1104 | 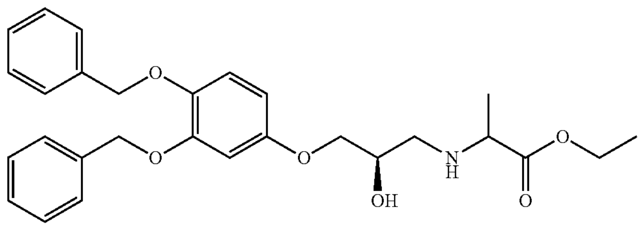 [SMILES: CCOC(=O)C(C)NC[C@@H](O)COc1ccc(OCc2ccccc2)c(OCc2ccccc2)c1] | Methyl (R)-(3-(3,4-bis(benzyloxy)phenoxy)-2-hydroxypropyl)glycineate |

The compounds were treated at different concentrations, and intracellular puncta of p62 or LC3, that is, the degree to which autophagosome was formed and p62 was delivered was observed by a confocal microscopy. The results are shown in FIG. 7. Immunofluorescence staining showed representative results from three or more independent experiments.

As shown in FIG. 7, it was confirmed that regardless of the concentration treated with the control compounds, the intracellular puncta of p62 protein was formed, the intracellular puncta and local co-existence of LC3 as an autophagosome marker were increased, and the intracellular puncta formation of LC3 was not increased.

Experimental Example 7. Evaluation of the Activity of P62-Mediated Delivery of Ubiquitinylated Proteins in Cultured Cells to Autophagy by Immunofluorescence Staining and Confocal Microscopy In order to confirm the activity level of P62-mediated delivery of ubiquitinylated proteins to autophagy in cultured cells after treatment with the compounds (Examples 1-19), immunofluorescence staining was performed in the same manner as in Experimental Example 4 by using p62 and FK2 as markers. As the compounds, YT-4-1, YT-4-2, YT-6-1, YT-6-7, YT-6-8, YOK-4404, YOK-1106, YOK-1107, YOK-1109, YOK-1204 and YOK-1204 were used. After treatment with the compounds, the intracellular puncta of p62 or FK2, that is, the extent to which p62 and ubiquitinated proteins were delivered to autophagosome, were observed by confocal microscopy. The results are shown in FIGS. 8a and 8b. Immunofluorescence staining showed representative results from three or more independent experiments.

As shown in FIGS. 8a and 8b, it was confirmed that after treatment with the p62 ligand compounds according to the present invention, intracellular punctae of FK2, markers of p62 protein and ubiquitination protein, were formed and the local co-existence of the punctae were increased.

Experimental Example 8. Evaluation of the Activity of P62-Mediated Delivery of Misfolded Huntingtin Proteins in Cultured Cells to Autophagy by Immunofluorescence Staining and Confocal Microscopy In order to confirm the activity level of P62-mediated delivery of misfolded huntingtin (Htt-Q103), a major protein of Huntington's disease, degenerative brain disease after treatment with the compounds (Examples 1-19), immunofluorescence staining was performed in the same manner as in Experimental Example 4 by using p62 and Htt-Q103-GFP as markers. As the compounds, YOK-1106, YOK-1107, YOK-1109, YOK-1204, YOK-2204, YOK-4404, YT-4-1, YT-4-2, YT-6-1, YT-6-7 and YT-9-1 were used. After treatment with the compounds, the intracellular puncta of p62 or Htt-Q103-GFP, that is, the extent to which p62 and misfolded huntingtin proteins were delivered to autophagosome, were observed by confocal microscopy. The results are shown in FIGS. 9a and 9b. Immunofluorescence staining showed representative results from three or more independent experiments.

As shown in FIGS. 9a and 9b, after treatment with the p62 compounds according to the present invention, intracellular puncta formation of FK2, markers of p62 protein and ubiquitination protein, and an increase in the local co-existence of the punctae were confirmed.

What is claimed is:
1. A p62 ligand compound of the following Chemical Formula 1 or a pharmaceutically acceptable salt thereof:

[Chemical Formula 1]

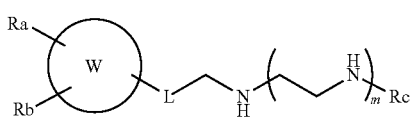

in Chemical Formula 1,
W is C6-C10 aryl;
n1 is an integer of 1 to 4;
m is an integer of 0 to 2;

$R_a$ is $R_1$ or $-OR_1$,
where $R_1$ is $(CH_2)_{n2}-R'_1$,
$R'_1$ is phenyl which is unsubstituted or substituted by hydroxy, halogen, $C_{1-4}$ alkyl', $C_{1-4}$ alkoxy, nitro, amino, $(C_{1-4}$ alkyl)amino, or di($C_{1-4}$ alkyl)amino,
n2 is an integer of 1 to 6;
$R_b$ is $-OR_2$,
where $R_2$ is hydrogen or $-(CH_2)_{n3}-R'_2$,
$R'_2$ is phenyl which is unsubstituted or substituted by hydroxy, halogen, $C_{1-4}$ alkyl, $C_{1-4}$ alkoxy, nitro, amino, $(C_{1-4}$ alkyl)amino, or di($C_{1-4}$ alkyl)amino,
n3 is an integer of 1 to 6;
$R_c$ is $-(CH_2)_{n4}-OH$, $-(CH_2)_{n4}-NH-C(=NH)NH_2$, $-C(=NH)NH_2$, $C_{1-6}$ alkyl, $-CH(R_3)-COO-R_4$, or $-CH(COO-R_4)-CH_2CH_2CH_2-NH-C(=NH)NH_2$, $-(CH_2)_{n4}-O-(CH_2)_{n4}-OR_4$, $-CONH(CH_2)_{n4}-OR_4$, $-CO(CH_2)_{n5}-OR_4$, $-(CH_2)_{n5}-CH(NH_2)-COOR_4$, $-(CH_2)_{n5}-CONHR_4$,
n4 is an integer of 2 to 4,
n5 is an integer of 1 to 4,
$R_3$ is hydrogen or $C_{1-4}$ alkyl,
$R_4$ is hydrogen, or $C_{1-4}$ alkyl, and
wherein the p62 ligand compound is optically pure (R) form, and
wherein the compound of Chemical Formula 1 is not a compound selected from the group consisting of the following compounds:
1) (R)-1-(3,4-(bis(benzyloxy)phenoxy)-3-((2-hydroxyethyl)amino)propan-2-ol (YOK-1106);
2) (R)-1-(3,4-(bis((4-chlorobenzyl)oxy)phenoxy)-3-((2-hydroxyethyl)amino)propan-2-ol (YT-6-1);
3) (R)-1-(3-((4-chlorobenzyl)oxy)phenoxy)-3-((2-hydroxyethyl)amino)propan-2-ol (YT-6-2);
4) (R)-1-(3-((4-chlorobenzyl)oxy)phenoxy)-3-((2-hydroxyethyl)amino)propan-2-ol (YT-6-7);
5) (R)-1-(3-((4-fluorobenzyl)oxy)phenoxy)-3-((2-hydroxyethyl)amino)propan-2-ol (YT-6-8);
6) (R)-1-(2-((3-(3,4-bis(benzyloxy)phenoxy)-2-hydroxypropyl)amino)ethyl)guanidine (YOK-1109);
7) (R)-1-(2-((3-(3,4-diphenethoxyphenoxy)-2-hydroxypropyl)amino)ethyl)guanidine (YOK-2209);
8) (R)-1-(2-((3-(3,4-bis(4-chlorobenzyl)oxy)phenoxy)-2-hydroxypropyl)amino)ethyl)guanidine (YT-9-1);
9) (R)-1-(2-((3-(3,4-bis(4-fluorobenzyl)oxy)phenoxy)-2-hydroxypropyl)amino)ethyl)guanidine (YT-9-2);
10) (R)-1-(3-(3,4-bis(benzyloxy)phenoxy)-2-hydroxypropyl)guanidine (YOK-1107);
11) (R)-1-(3-(3,4-diphenethoxyphenoxy)-2-hydroxypropyl)guanidine (YOK-2207);
12) (R)-1-(3,4-bis(benzyloxy)phenoxy)-3-(isopropylamino)propan-2-ol (YOK-1104);
13) (R)-1-(3,4-diphenethoxyphenoxy)-3-(isopropylamino)propan-2-ol (YOK-2204);
14) (R)-1-(3,4-bis(3-phenylpropoxy)phenoxy)-3-(isopropylamino)propan-2-ol (YOK-3304);
15) (R)-1-(3,4-bis(4-phenylbutoxy)phenoxy)-3-(isopropylamino)propan-2-ol (YOK-4404);
16) (R)-1-(4-(benzyloxy)-3-phenethoxyphenoxy)-3-(isopropylamino)propan-2-ol (YOK-1204);
17) (R)-1-(4-(benzyloxy)-3-(3-phenylpropoxy)phenoxy)-3-(isopropylamino)propan-2-ol (YOK-1304);
18) (R)-1-(3,4-bis((4-chlorobenzyl)oxy)phenoxy)-3-(isopropylamino)propan-2-ol (YT-4-1); and
19) (R)-1-(3,4-bis((4-fluorobenzyl)oxy)phenoxy)-3-(isopropylamino)propan-2-ol (YT-4-2).

2. The compound or a pharmaceutically acceptable salt thereof according to claim 1, wherein the W is phenyl, and n1 is 1 or 2.

3. The compound or a pharmaceutically acceptable salt thereof according to claim 1, wherein the $R_a$ is hydrogen or $-O-(CH_2)_{n2}-R'_1$, $R'_1$ is phenyl that is unsubstituted or substituted by hydroxy, fluoro, chloro, bromo, methyl, ethyl, methoxy, ethoxy, nitro, amino or dimethylamino, and n2 is an integer of 1 to 4.

4. The compound or a pharmaceutically acceptable salt thereof according to claim 1, wherein the $R_b$ is hydroxy, or $-O-(CH_2)_{n3}-R'_2$, $R'_2$ is phenyl which is unsubstituted or substituted by hydroxy, fluoro, chloro, bromo, methyl, ethyl, methoxy, ethoxy, nitro, amino or dimethylamino, and n3 is an integer of 1 to 4.

5. The compound or a pharmaceutically acceptable salt thereof according to claim 1, wherein the $R_c$ is is $-(CH_2)_{n4}-OH$, $-(CH_2)_{n4}-NH-C(=NH)NH_2$, $-C(=NH)NH_2$, methyl, ethyl or isopropyl, and n4 is an integer of 2 to 3.

6. A p62 ligand compound or a pharmaceutically acceptable salt, wherein the compound is selected from the group consisting of the following compounds 1) to 19):
1) (R)-1-(3,4-(bis(benzyloxy)phenoxy)-3-((2-hydroxyethyl)amino)propan-2-ol (YOK-1106);
2) (R)-1-(3,4-(bis((4-chlorobenzyl)oxy)phenoxy)-3-((2-hydroxyethyl)amino)propan-2-ol (YT-6-1);
3) (R)-1-(3-((4-chlorobenzyl)oxy)phenoxy)-3-((2-hydroxyethyl)amino)propan-2-ol (YT-6-2);
4) (R)-1-(3-((4-chlorobenzyl)oxy)phenoxy)-3-((2-hydroxyethyl)amino)propan-2-ol (YT-6-7);
5) (R)-1-(3-((4-fluorobenzyl)oxy)phenoxy)-3-((2-hydroxyethyl)amino)propan-2-ol (YT-6-8);
6) (R)-1-(2-((3-(3,4-bis(benzyloxy)phenoxy)-2-hydroxypropyl)amino)ethyl)guanidine (YOK-1109);
7) (R)-1-(2-((3-(3,4-diphenethoxyphenoxy)-2-hydroxypropyl)amino)ethyl)guanidine (YOK-2209);
8) (R)-1-(2-((3-(3,4-bis(4-chlorobenzyl)oxy)phenoxy)-2-hydroxypropyl)amino)ethyl)guanidine (YT-9-1);
9) (R)-1-(2-((3-(3,4-bis(4-fluorobenzyl)oxy)phenoxy)-2-hydroxypropyl)amino)ethyl)guanidine (YT-9-2);
10) (R)-1-(3-(3,4-bis(benzyloxy)phenoxy)-2-hydroxypropyl)guanidine (YOK-1107);
11) (R)-1-(3-(3,4-diphenethoxyphenoxy)-2-hydroxypropyl)guanidine (YOK-2207);
12) (R)-1-(3,4-bis(benzyloxy)phenoxy)-3-(isopropylamino)propan-2-ol (YOK-1104);
13) (R)-1-(3,4-diphenethoxyphenoxy)-3-(isopropylamino)propan-2-ol (YOK-2204);
14) (R)-1-(3,4-bis(3-phenylpropoxy)phenoxy)-3-(isopropylamino)propan-2-ol (YOK-3304);
15) (R)-1-(3,4-bis(4-phenylbutoxy)phenoxy)-3-(isopropylamino)propan-2-ol (YOK-4404);
16) (R)-1-(4-(benzyloxy)-3-phenethoxyphenoxy)-3-(isopropylamino)propan-2-ol (YOK-1204);
17) (R)-1-(4-(benzyloxy)-3-(3-phenylpropoxy)phenoxy)-3-(isopropylamino)propan-2-ol (YOK-1304);
18) (R)-1-(3,4-bis((4-chlorobenzyl)oxy)phenoxy)-3-(isopropylamino)propan-2-ol (YT-4-1); and
19) (R)-1-(3,4-bis((4-fluorobenzyl)oxy)phenoxy)-3-(isopropylamino)propan-2-ol (YT-4-2).

7. A composition comprising a compound of Chemical Formula 1 according to claim 1 or a pharmaceutically acceptable salt thereof.

8. The composition according to claim 7, wherein the composition is a pharmaceutical composition.

9. The composition according to claim 7, wherein the composition is a food composition.

10. A composition comprising a compound according to claim 6, a pharmaceutically acceptable salt, or stereoisomer thereof.

11. The composition according to claim 10, wherein the composition is a pharmaceutical composition.

12. The composition according to claim 10, wherein the composition is a food composition.

* * * * *